US006168807B1

(12) United States Patent
Dupont et al.

(10) Patent No.: US 6,168,807 B1
(45) Date of Patent: Jan. 2, 2001

(54) LOW MOLECULAR WEIGHT COMPONENTS OF SHARK CARTILAGE, PROCESSES FOR THEIR PREPARATION AND THERAPEUTIC USES THEREOF

(75) Inventors: Éric Dupont; Yves Lachance, both of Saint Nicolas; Denis Lessard; Serge Auger, both of Lévis, all of (CA)

(73) Assignee: Les Laboratoires Aeterna Inc., Quebec (CA)

( * ) Notice: Under 35 U.S.C. 154(b), the term of this patent shall be extended for 0 days.

(21) Appl. No.: 09/122,481

(22) Filed: Jul. 23, 1998

(51) Int. Cl.$^7$ .................................................. C01B 31/04

(52) U.S. Cl. ............................................................. 424/548

(58) Field of Search ............................................. 424/548

(56) References Cited

U.S. PATENT DOCUMENTS

| | | | |
|---|---|---|---|
| Re. 28,093 | 7/1974 | Balassa | 424/548 |
| 3,478,146 | 11/1969 | Balassa | 424/548 |
| 3,966,908 | 6/1976 | Balassa | 424/548 |
| 4,042,457 | 8/1977 | Kuettner et al. | 424/548 |
| 4,212,857 | 7/1980 | Balassa et al. | 424/548 |
| 4,243,582 | 1/1981 | Spilburg et al. | 530/395 |
| 4,350,682 | 9/1982 | Balassa | 424/64 |
| 4,356,261 | 10/1982 | Kuettner | 435/70.2 |
| 4,444,752 | 4/1984 | Prudden | 424/548 |
| 4,456,589 | 6/1984 | Holman et al. | 424/548 |
| 4,469,676 | 9/1984 | Hecmati | 424/548 |
| 4,473,551 | 9/1984 | Schinitsky | 424/548 |
| 4,656,137 | 4/1987 | Balassa | 435/267 |
| 4,746,729 | 5/1988 | Kuettner et al. | 530/353 |
| 4,749,522 | 6/1988 | Kamarei . | |
| 4,822,607 | 4/1989 | Balassa et al. | 424/548 |
| 5,075,112 | 12/1991 | Lane | 42/434 |
| 5,618,925 | 4/1997 | Dupont et al. | 530/400 |
| 5,843,920 | * 12/1998 | Weisz | 514/58 |

FOREIGN PATENT DOCUMENTS

| | | |
|---|---|---|
| 45-001444 | * 1/1970 | (JP) . |
| 59-039828 | * 3/1984 | (JP) . |
| 60-178820 | * 9/1985 | (JP) . |
| 9309766 | 5/1993 | (WO) . |
| 9412510 | 6/1994 | (WO) . |
| 9503036 | 2/1995 | (WO) . |
| 9532722 | 12/1995 | (WO) . |
| 9623512 | 8/1996 | (WO) . |
| 9716197 | 5/1997 | (WO) . |

OTHER PUBLICATIONS

Scott et al., "Selective Demineralization of Hard Tissues in Organic Solvents: Retention or Extraction of Proteoglycan?", J. Microsc., 134(3), pp. 291–297, 1983.
Pavia et al., "Introduction of Organic Laboratory Techniques a Contemporary Approach", 2nd Ed., Saunders College Publishing, Phildelphia, pp. 500–501, 1982.
Burkick & Jackson, "High Purity Solvent Guide", 2nd Ed., Burdick & Jackson Laboratories, Inc., pp. 128–137, 1982.

Oikawa, T., H. Ashino–Fuse, M. Shimamura, U. Koide and T. Kwaguchi, "A novel angiogenic inhibitor derived from Japanese shark cartilage (I). Extraction and estimation of inhibitory activities toward tumor and embryonic angiogenesis," *Cancer Letters*, 51 (1990) 181–186.
Folkman, Judah and Michael Klagsbrun, "Angiogenic Factors," *Science*, vol. 235, 442–446.
Luer, C. A., "Inhibitors of Angiogenesis from Shark Cartilage, " Fed. Proc. 45(4): 949.
Suzuki, Fujio, Masaharu Takigawa, Yugi Hiraki, Yukio Kato, Keisuke Fukuo, Tsuyoshi Shiio and Yasumi Yugari, "Cartilage–derived Antitumor Factor (CATF): A High Molecular Weight Fraction Cartilage Extract Inhibits Solid Tumor Growth," *Journal of Bone and Mineral Metabolism*, 1984 vol. 2 No. 3, 53–57.
Langer, Robert, Henry Brem, Kenneth Falterman, Michael Klein, Judah Folkman, "Isolation of a Cartilage Factor That Inhibits Tumor Neovascularization," *Science*, vol. 193, 70–72.
Sorgente, Nino, Ph.D., Klaus E. Kuettner, Ph.D., Lawrence W. Soble, M.S., and Reuben Eisenstein, M.D., "The Resistance of Certain Tissues to Invasion," *Laboratory Investigation*, vol. 32, No. 2, 1975, p. 217–222.
Brem, Henry and Judah Folkman, "Inhibitions of Tumor Angiogenesis Mediated by Cartilage," *The Journal of Experimental Medicine*, vol. 141, 1975, p. 427–439.
Kuettner, Klaus E., Lawrence Soble, Richard L. Croxen, Barbara Marczynska, Judith Hiti, and Elvin Harper, "Tumor Cell Collagenase and Its Inhibition by a Cartilage–Derived Protease Inhibitor," *Science*, ol. 196, p. 653–654.

(List continued on next page.)

*Primary Examiner*—Jon P. Weber
(74) *Attorney, Agent, or Firm*—Akin, Gump, Strauss, Hauer & Feld, L.L.P.

(57) ABSTRACT

This invention relates to a process by which organic solvent-containing solutions are used in lieu of pure water for the preparation of cartilage extracts and fractions thereof. Different organic solvents have been tested for the preparation of extracts containing biologically active components possessing at least an activity against a matrix metalloprotease (anti-MMP). This invention also relates to a process by which a total liquid extract of shark cartilage composed of molecules having molecular weights less than about 500 kDa (0-500 fraction) is purified into two well separated fractions composed of molecules having molecular weights less than about 1 kDa (0-1 fraction) and between about 1 to 500 kDa (1-500 fraction). In order to prevent the formation of aggregates, to improve the dissolution and the stability of active components, sucrose or other stabilizing agents can be added. The 0-500 fraction, the 0-1 fraction and the 1-500 fraction as well as their equivalents containing 1% w/v sucrose possess have anti-MMP and anti-tumor activities. The invention also provides a component which has at least anti-MMP and anti-tumor activities, and which has a mass of 244 amu (atomic mass unit). The use of the above extracts, derived fractions or components for inhibiting MMP enzyme, neovascularization and/or metastase formation is also described.

17 Claims, 10 Drawing Sheets

OTHER PUBLICATIONS

Langer, Robert, Henry Brem, Kenneth Falterman, Michael Klein, and Judah Folkman, "Isolation of a Cartilage Factor That Inhibits Tumor Neovascularization," *Science*, vol. 193, p. 70–72.

Sadove, Alan Michael, MD, MS and Klaus E. Kuettner, Ph.D., "Inhibition of Mammary Carcinoma Invasiveness with Cartilage–Derived Inhibitor," *Orthopaedic Surgery*, p. 499–501.

Paull, Bendicht U., Vincent A. Memoll, And Klaus E. Kuettner, "Regulation of Tumor Invasion by Cartilage–Derived Anti–Invasion Factor in Vitro," *JNCI*, vol. 67, No. 1, Jul. 1981, p. 65–73.

Morales, T.I., K. E. Kuettner, D. S. Howell and J. F. Woessner, "Characterization of the Metalloproteinase Inhibitor Produced by Bovine Articular Chondrocyte Cultures," *Biochimic et Biophysica Acta*, 760 (1983), p. 221–229.

Moses, Marsha A., Judith Sudhalter and Robert Langer, "Identification of an Inhibitor of Neovascularization from Cartilage," *Science*, vol. 248, p. 1408–1410.

Moses, Marsha A. and Robert Langer, "A Metalloproteinase Inhibitor as an Inhibitor of Neovascularization," *Journal of Cellular Biochemistry*, vol. 47, 1991, p. 230–235.

Moses, M. A., "A Cartilage–Derived Inhibitor of Neovascularization and Metalloprotteinases," *Clinical and Experimental Rheumatology 11 (Supp. 8)*, 1993, p. S67–S69.

Moses, Marsha A. and Robert Langer, "Metalloproteinase Inhibition as a Mechanism for the Inhibition of Angiogenesis," *Angiogenesis: Key Principles—Science—Technology—Medicine*, 1992, p.146–151, Ed., Steiner, et al, Birkhauser Verlag.

McGuire, Timothy R., Peter W. Kazakoff, Eric B. Hoie, and Margery A. Fienhold, "Antiproliferative Activity of Shark Cartilage With and Without Tumor Necrosis Factor–α in Human Umbilical Vein Endothelium," *Pharmacotherapy*, 1996;16(2), p.237.

Lee, Anne and Robert Langer, "Shark Cartilage Contains Inhibitors of Tumor Angiogenesis," *Science*, vol. 221, p. 1185–1187.

Davis, Paul F., Yi He, Richard H. Furneaux, Peter S. Johnston, Beate M. Ruger and George C. Slim, "Inhibition of Angiogenesis by Oral Ingestion of Powdered Shark Cartilage in a Rat Model," *Microvascular Research*, vol. 54 (1997), p. 178–182.

Mathews, James, "Media Feeds Frenzy Over Shark Cartilage As Cancer Treatment," *Journal of the National Cancer Institute*, vol. 85, No. 15, Aug. 4, 1993, p. 1190–1191.

* cited by examiner-

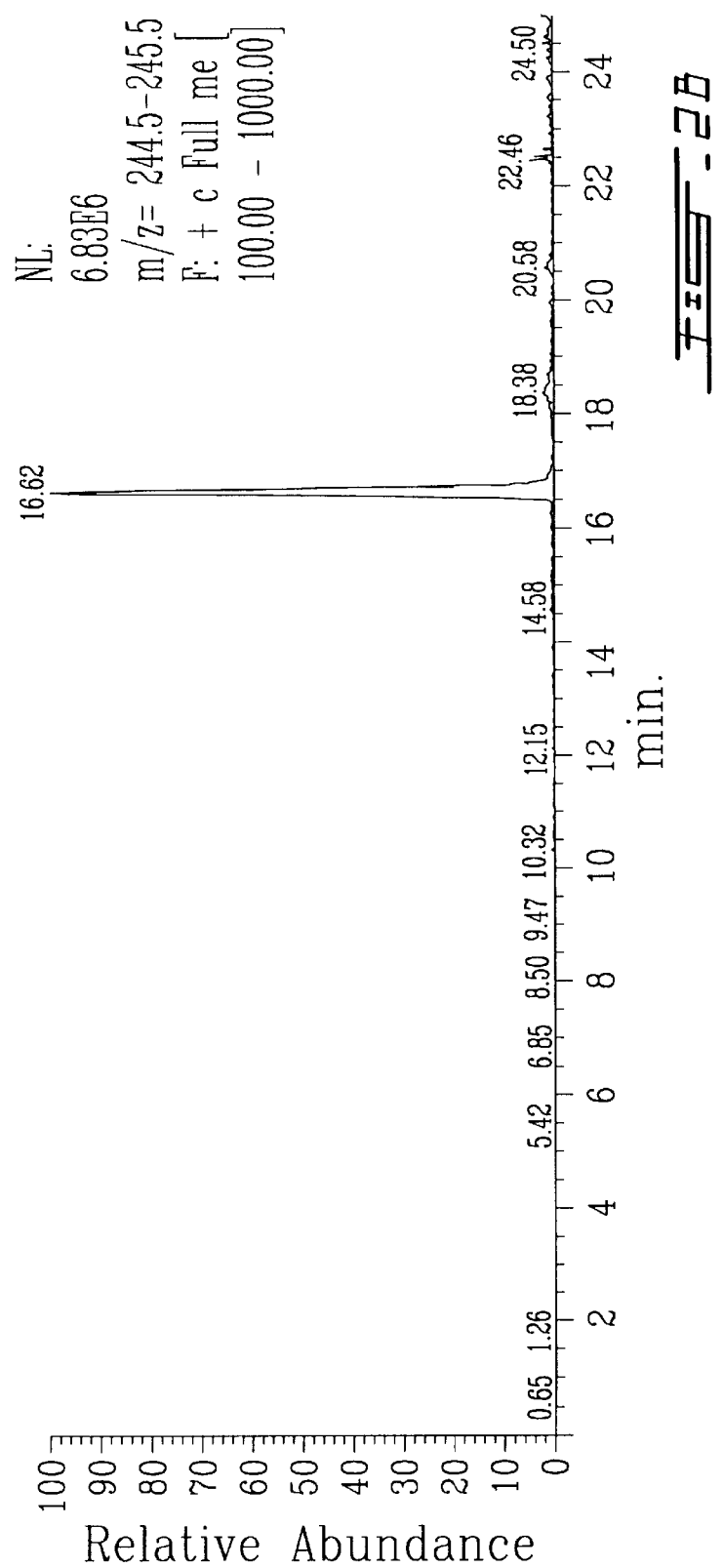

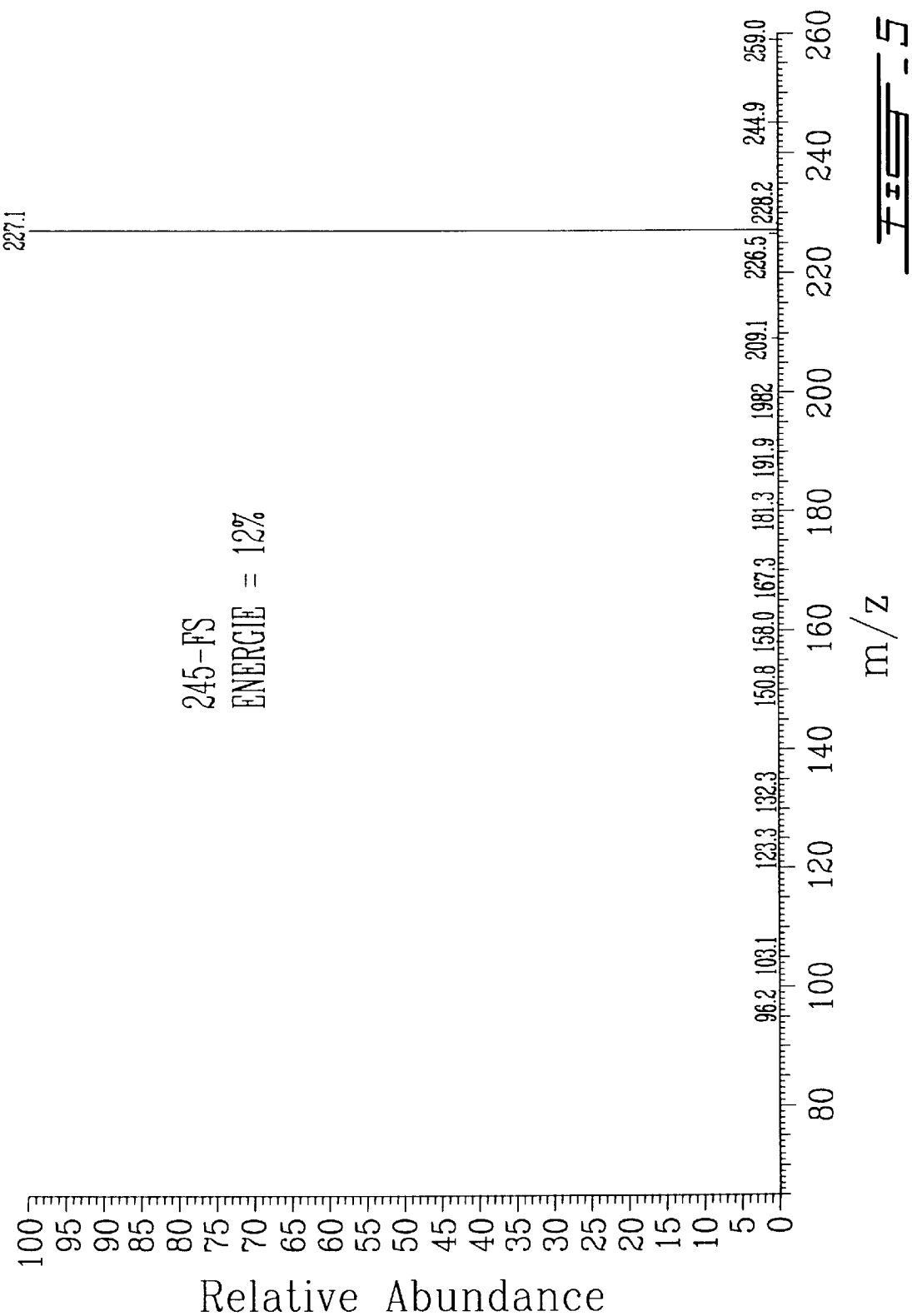

LOW MOLECULAR WEIGHT COMPONENTS OF SHARK CARTILAGE, PROCESSES FOR THEIR PREPARATION AND THERAPEUTIC USES THEREOF

FIELD OF THE INVENTION

This invention relates to low molecular weight components extracted from shark cartilage and to processes for their preparation. This invention also relates to processes for isolating and purifying a cartilage extract under a variety of conditions. The low molecular weight components exhibit at least one of anti-matrix metalloprotease (anti-MMP), anti-angiogenic and anti-tumor activities.

BACKGROUND OF THE INVENTION

Processes for the preparation of shark cartilage extracts and the extracts themselves are disclosed in International Publications WO 95/32722, WO 96/23512 and WO 97/16197. Liquid extracts of shark cartilage have been tested in various assays for antiangiogenic, anticollagenolytic, direct anti-tumor proliferating and anti-inflammatory activities.

WO 95/32722 discloses a process for obtaining a shark cartilage extract having antiangiogenic, in vitro direct anti-tumor proliferating and in vivo anti-tumor activities. That process comprises the steps of blending shark cartilage tissue and reducing the same to a particle size of about 500 μm in water; extracting active components into the water; and fractionating the extracts so obtained in order to recover molecules having molecular weights less than about 500 kDa (0-500 fraction). The liquid cartilage extract was concentrated on a membrane having a nominal porosity of about 1 kDa to form a concentrated liquid extract comprising molecules having molecular weights less than about 500 kDa. The extract was enriched in molecules having molecular weights between about 1–500 kDa. The 0-500 fraction was further fractionated to form a plurality of extracts containing anti-tumor proliferating molecules having molecular weights extending from about 1 to 120 kDa. The WO 95/32722 Publication does not disclose the specific recovery of components having molecular weights less than about 1 kDa. It also does not disclose a process of obtaining a cartilage extract or fractions thereof in organic solvent-containing solutions.

International Publication No. WO 96/23512 discloses a process for extracting biologically active components from any source of cartilage in aqueous solutions. Further, this publication discloses other biological activities associated with the liquid shark cartilage, namely anticollagenolytic and anti-inflammatory activities. The WO 96/23512 Publication does not disclose the recovery of components having molecular weights less than about 1 kDa nor any process making use of organic solvent-containing solutions.

International Publication No. WO 97/16197 discloses a process for the recovery of an aqueous extract enriched in molecules having molecular weights between about 0.1 to 500 kDa. Although that process may recover components having molecular weights of less than about 1 kDa, it does not provide for any recovery of specific low molecular weight components. No component in an isolated or purified form is disclosed.

It is generally accepted in the art that matrix metalloproteases are involved in the processes of neovascularization, promoting the growth of primary tumors and in the formation of metastases. Accordingly, compounds or agents exhibiting antiangiogenic and/or anti-matrix metalloprotease activities are believed to be useful for at least one of inhibiting neovascularization, inhibiting growth in tumors, inhibiting metastatic invasion of cells, inhibiting formation of metastases and treating angiogenesis related diseases.

Given the interest in components obtained from shark cartilage, there exists the need for improved processes for their preparation and for the isolation and purification of other components not previously known to possess biological activity.

SUMMARY OF THE INVENTION

The present invention seeks to provide improved processes for the preparation of extracts obtained from shark cartilage.

In one aspect, the present invention provides a process wherein a variety of conditions are used for the preparation of cartilage extracts and fractions thereof containing biologically active components. In one embodiment, the invention provides a process for the preparation of shark cartilage extracts having components possessing at least an anti-MMP (anti-matrix metalloprotease) activity.

In another aspect, the present invention provides a process by which the 0-500 molecular weight fraction of biologically active components derived from a cartilage liquid extract is separated into two separate fractions wherein the first fraction comprises components having molecular weights less than about 1 kDa (0-1 fraction) and the second fraction comprises components having molecular weights between about 1 to 500 kDa (1-500 fraction).

In order to minimize the formation of component aggregates, to improve the dissolution and the maintenance of a, stable, soluble form, sucrose or one or more other suitable stabilizers such as dextran, Ficoll™, fructose, gelatin, glucose, glycine, inositol, lactose, mannitol and sorbitol can be added in a sufficient stabilizing amount to any of the 0-500, 0-1 and 1-500 fractions, or can be used in any step of the manufacturing process. As used herein in reference to fractions, solutions or extracts, the phrase "containing 1% w/v sucrose" refers to a respective fraction, solution or extract containing about 1% w/v sucrose. Biologically active components in the 0-1 and 1-500 fractions possess anti-MMP, antiangiogenic and anti-tumor activities.

In another aspect, the present invention provides a shark cartilage derived component having a molecular weight of about 244 amu (atomic mass unit), herein termed Æ-986, possessing at least one of anti-MMP and anti-tumor activities. The process and materials used for the purification of the Æ-986 reveal some physico-chemical characteristics of the latter, which are responsible for the partitioning of this component in different solvent phases and chromatographic systems. The present invention also provides a process for the isolation and purification of the Æ-986 component or of an equivalent component obtained from any source of cartilage.

Yet another aspect of the invention provides a purified biologically active compound derived from any source of cartilage which corresponds to the compound having a molecular weight of about 244 amu isolated from shark cartilage and possessing anti-MMP and anti-tumor activities.

Still another aspect of the invention provides a method of inhibiting a MMP enzyme, which method comprises the step of contacting a substrate cleavable by said enzyme with an effective amount of one or more cartilage extracts or fractions derived therefrom or the Æ-986 component prepared according to the present invention.

Still other aspects of the invention provide methods of inhibiting neovascularization and the formation of metastases, which methods comprise the step of contacting a target tissue with an effective amount of a cartilage derived extract, solution, homogenate, suspension, fraction such as the 0-500 fraction, the 0-1 fraction, the 1-500 fraction or the same fractions containing 1% w/v sucrose, or component such as the Æ-986 component.

BRIEF DESCRIPTION OF THE DRAWINGS

The following figures are part of the present specification and are included to further demonstrate certain aspects of the invention. The invention may be better understood by reference to one or more of these figures in combination with the detailed description of the specific embodiments presented herein.

FIGS. 2a and 2b depict the total ion chromatogram as well as the single ion chromatogram (245 M+1) obtained from analysis of the Æ-986 on an HPLC C18 system using an ammonium formate buffer (pH 3) and gradient elution.

FIG. 5 depicts the MS/MS spectrum of the Æ-986 showing the loss of 18 amu (major peak m/e 227.1) which corresponds to loss of a water molecule.

DETAILED DESCRIPTION OF THE INVENTION

Biological Assays

Figure 1A:
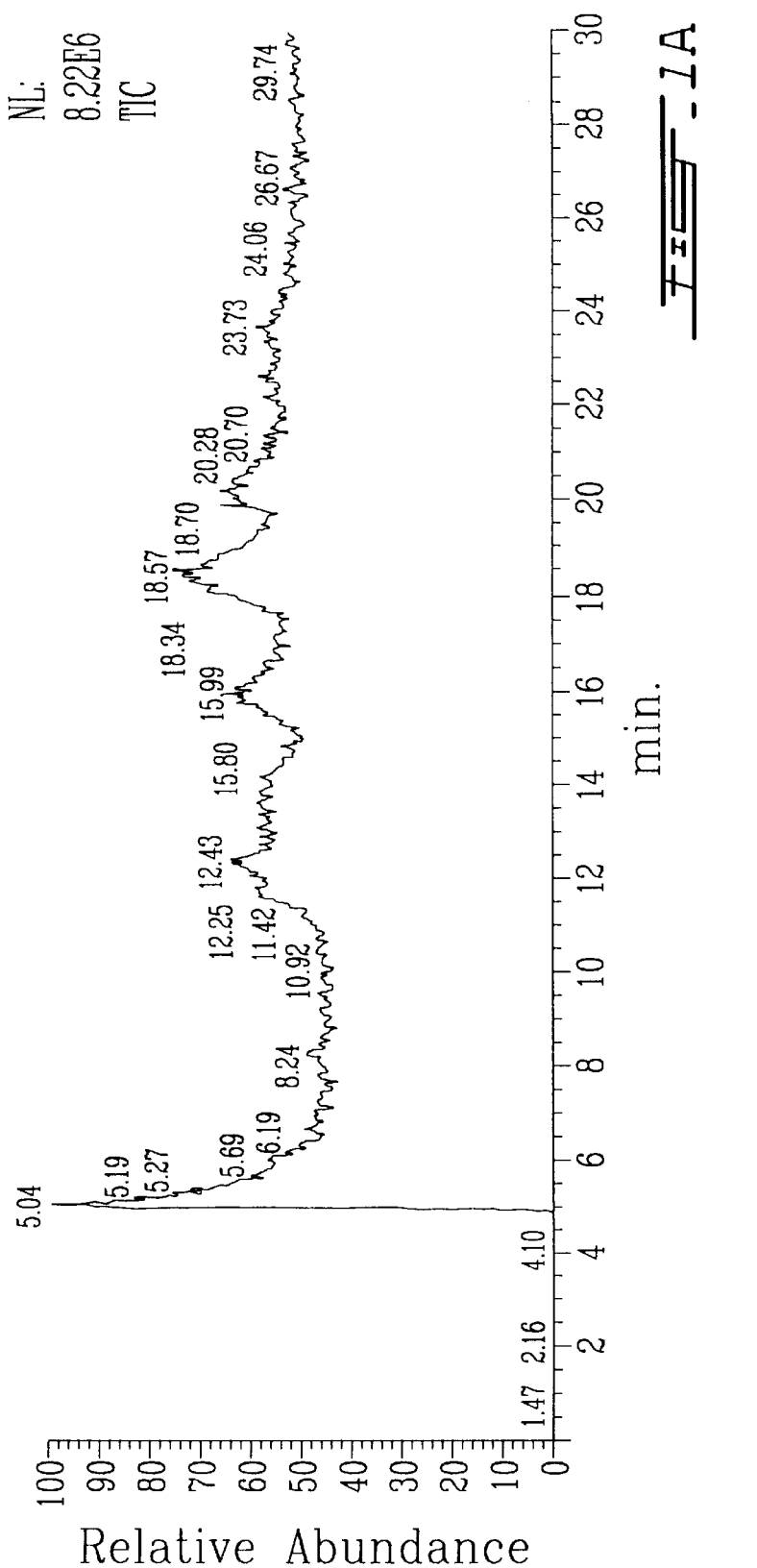
FIGS. 1a and 1b depict the total ion chromatogram as well as the single ion chromatogram (245 M+1) obtained from analysis of the Æ-986 on an HPLC C18 system using an ammonium formate buffer (pH 7) and isocratic elution.

The biological properties of shark cartilage extracts, of fractions derived therefrom and of the component Æ-986 were determined by using at least one of the following assays:

Gelatinase Inhibition Assay (GIA): an assay for evaluating anti-MMP activity;

Embryonic Vascularisation Test (EVT): an assay for evaluating antiangiogenic activity; and Lewis Lung Carcinoma metastatic mouse model (LLC): an assay for evaluating anti-tumor activity.

GIA

The GIA was performed using a commercial kit (Boehringer Mannheim). The GIA is used to determine the ability of components in the cartilage derived extracts, or fractions thereof or of the Æ-986 component to inhibit the activity of the gelatinase A enzyme (MMP-2).

Briefly, the GIA was performed as follows. A biotin-labeled gelatine substrate was incubated with gelatinase A in the absence or the presence of a liquid cartilage extract or its derivatives. Subsequently, the reaction mix was loaded onto a streptavidin-coated microtiter plate. The biotin-labeled gelatine was bound to the streptavidin-coated microtiter via its free biotin residues. If the substrate, gelatine, was not spliced by gelatinase, a streptavidin-peroxidase (POD) conjugate bound to the gelatinase-biotin-complex. The POD then converted an added ABTS substrate to a green end product, which was measured at 405 nm. However, if the biotin-labeled gelatine was spliced by gelatinase, only small fragments of gelatine were formed. These fragments, after attachment to a microtiter plate, did not possess the ability to bind the streptavidin-POD conjugate; and therefore, no color reaction occurred.

High gelatinase activity thereby yields low signals, and a low gelatinase activity in turn (e.g. by addition of an inhibitor) causes high signals. The activity sought for the components in a cartilage derived extract, or fractions derived therefrom, may be an inhibitory activity towards gelatinase or an antagonist activity which competes with the interaction between gelatinase and its gelatine substrate (e.g. the antagonist components bind gelatine).

EVT

The Embryonic Vascularization Test (EVT) was performed to determine the ability of components in the shark cartilage liquid extracts, or fractions derived therefrom, to inhibit the formation of new blood vessels (antiangiogenic activity).

The normal development of a chick embryo involves the formation of an external vascular system located in the vitelline membrane which carries nutrients from the vitellus (yolk) to the developing embryo. When placed onto the vitelline membrane, antiangiogenic substances can inhibit the blood vessel formation that occurs in the vitelline membrane.

Methylcellulose discs (an inert solid and transparent matrix) containing different quantities of components from shark cartilage derived liquid extracts, or fractions derived therefrom or appropriate controls were placed on the external border of the vascular perimeter of the vitelline membrane, where the angiogenic process occurs. Positive controls consisted of methylcellulose discs containing 1.5 mg/ml of 2-Methoxyestradiol. Control and sample-containing discs were placed onto the vitelline membrane of 3 day-old embryos. At this point, only beginnings of the main blood vessels are invading the vitellus. Methylcellulose discs containing a negative control or an amount of components from shark cartilage derived liquid extract or fractions derived therefrom were always placed on the vitelline membrane of the same embryo concurrently. Both discs were arranged in a symmetric fashion with respect to the cephalo-caudal axis of the embryo in order to minimize inter individual variations when comparing the efficacy of said components to that of negative controls. Vascularization was assessed 24 hours after disc deposition, and results were expressed as the percent of embryos in which blood vessel formation was affected. The blood vessel formation was considered affected when its growing path was either deviated, or diminished or when there was no growth observed beyond the disc as compared to the negative control.

LLC Model

The Lewis Lung Carcinoma mouse model (LLC) was used to determine the ability of components of shark cartilage liquid extracts, or of fractions derived therefrom or of the Æ-986, to inhibit the formation of metastases within lung.

Cell culture: The Lewis lung carcinoma clone M27, with a high metastatic potential to the lung, was established by Dr P. Brodt (Brodt P, Cancer Res., 46: 2442,1986). This model is well established and is known for its predictive correlation between in vitro and in vivo activity. Cells were maintained in RPMI-1640 medium supplemented with 10% fetal bovine serum and 1% penicillin-streptomycin, under 5% $CO_2$ and were passaged twice a week. Stocks of the cells were generated and stored as early passages. All experiments were carried out using the same passage. For tumor induction, M27 cells were grown at 70% confluence in complete medium and then collected using trypsin-EDTA solution (0.05% trypsin, 0.53 mM EDTA-4Na in HBSS without $Ca^{++}$ or Mg++). Cells were then centrifuged, washed and resuspended ($1 \times 10^6$ LLC cells per 200 μl of PBS $Ca^{++}$ and $Mg^{++}$ free). Viability was examined by tryptan blue staining and only flasks in which the viability was superior to 95% were used for inoculation.

Tumor Induction: C57BL/10 female mice (15 to 20 g) (Charles River Inc.) were used to induce the Lewis lung carcinoma tumors. After one week of incubation, LLC cells were transplanted subcutaneously ($5 \times 10^5$ viable cells per 100 μl) in the axillary region of the right flank at day 0. All animals were inoculated at the same site. Tumor growth was monitored every day using calipers. The relative tumor volume was calculated using the formula: length (cm)× [width $(cm)]^2/2$ where the length corresponds to the longest axis and the width corresponds to the perpendicular shortest axis of the tumor. When the primary tumor reaches a size of 0.5–1.0 $cm^3$ (day 10 post-inoculation), mice bearing primary tumors of approximately identical size were randomly assigned to specific experimental groups of 15 animals each and labeled by numbers using the ear punching method. Surgery was performed under sterile conditions. Following a small skin incision (0.5–1 cm), the tumor was carefully separated from the surrounding healthy tissues. LLC cells (at early stage of growth) form a well localized tumor and separation was easy to achieve without any significant damage to normal tissues. Stereoscopic examination revealed the absence of any macroscopic residual tumor at the site of tumor inoculation and tumor regrowth was not observed under our conditions. Following removal, tumor was weighted and the wound was closed with surgical stainless steel clips and disinfected with providone-iodine.

Efficacy Study Experimental Design: Treatment with different test samples (components derived from shark cartilage liquid extracts, fractions derived therefrom or Æ-986) started the day following tumor removal (day 11 post-inoculation). Saline or the cartilage-derived products were given daily for two weeks by oral gavage. Oral gavage (0.5 ml) was performed using a 22G curved needle. As previous experiments had shown that a period of approximately two weeks after removal of the primary tumor was sufficient to obtain an average of 30 to 50 nodules on the lung surface, animals were sacrificed in a $CO_2$ chamber two weeks later. Following autopsy, both lungs were removed, weighed and fixed in 10% Bouin's fixative. Lung surface metastases were counted using a stereomicroscope (4×).

Measurement of body weight: Body weight was monitored every second or third day until sacrifice.

Processes for Preparing Cartilage Extracts
Extraction of Active Components from Shark Cartilage Using Organic Solvent-Containing Solutions The present invention provides a method of preparing a cartilage extract and of obtaining, isolating or purifying therefrom biologically active components therein, wherein at least a portion of the biologically active component is not of a protein nature. However, chaotropic agents which are useful for extracting protein-containing components may be used in the process of the present invention.

As used herein, the term "organic solvent-containing solution" refers to a solution or mixture comprising at least a portion of organic solvent. The organic solvent-containing solution can comprise one or more organic solvents and can contain water. An organic solvent or combination of organic solvents used herein is preferably polar. In one embodiment, at least one of methanol and ethanol can be used for the preparation of shark cartilage liquid extracts. Other organic solvents such as acetonitrile, propanol, isopropanol and acetone are suitable polar solvents that can be used. The organic solvent can include one or more halogenated, ether, protic, aprotic, polar, apolar, basic, acidic, hydrophobic, and hydrophilic solvents.

Suitable halogenated solvents include: chloroform, dibromomethane, butyl chloride, dichloromethane.

Suitable ether solvents include: dimethoxymethane, tetrahydrofuran, diethyl ether, ethylene glycol dimethyl ether, ethylene glycol diethyl ether, diethylene glycol diethyl ether, triethylene glycol dimethyl ether, t-butyl ethyl ether, or t-butyl methyl ether.

Suitable protic solvents may include, by way of example and without limitation,, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable aprotic solvents may include, by way of example and without limitation, dimethylformamide (DMF), dimethylacetamide (DMAC), 1,3-dimethyl-3,4,5,6-tetrahydro-2 (1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, acetone, ethyl methyl ketone, ethyl acetate, sulfolane, N,N-dimethylpropionamide, tetramethylurea, nitromethane, nitrobenzene, or hexamethylphosphoramide.

Suitable basic solvents include: 2-, 3-, or 4-picoline, pyrrole, pyrrolidine, morpholine, pyridine, or piperidine.

Suitable acidic solvents include trifluoroacetic acid, acetic acid, proprionic acid or formic acid.

Suitable hydrocarbon solvents include: benzene, cyclohexane, pentane, hexane, toluene, cycloheptane, methylcyclohexane, heptane, ethylbenzene, octane, indane, nonane, or naphthalene.

The organic solvent-containing solution can comprise combinations of organic solvents and/or combinations of organic solvents and water. Suitable protic solvent combinations with water can include, by way of example and without limitation, water-methanol, water-propanol, water-isopropanol, water-butanol. Suitable aprotic solvent combinations with or without water can include, by way of example and without limitation, water-acetonitrile, water-dimethylsulfoxide, methanol-acetonitrile, methanol-dimethylsulfoxide, ethanol-acetonitrile, and ethanol-dimethylsulfoxide.

The amount of organic solvent present in the invention can vary according to the nature or physical properties of a component to be extracted from cartilage. In general, the organic solvent-containing solution will contain about 1–100% v/v, about 40–80% v/v, at least 1% v/v, at least 10% v/v, at least 25% v/v, at least 50% v/v, at least 90% v/v or at least 99% v/v organic solvent with respect to the total solution volume.

Accordingly, the present invention provides a process for the preparation of extracts of shark cartilage comprising the steps of:

a) treating shark cartilage material with a quantity of organic solvent-containing solution to form a first mixture comprising soluble components of shark cartilage;

b) separating said first mixture to form a first liquid extract comprising said soluble components and a first mass of solids; and c) removing the organic solvent from said first liquid extract.

The process can further comprise the steps of:

d) removing a sufficient amount of liquid from said first liquid extract to form a substantially dry second mass of solids;

e) adding water to said second mass of solids to form a second mixture; and f) separating said second mixture to form a first final liquid extract and a third mass of solids.

The first mass of solids containing the shark cartilage material can be extracted an additional one or more times with an organic solvent-containing solution, or water in place of the organic solvent containing solution, according to the steps a) through c) described above to form second and third or further final liquid extracts containing at least residual amounts of soluble components of shark cartilage.

The separation of solids and liquid in step b) can be conducted according to any of a number of methods known to those of skill in the art including, by way of example and without limitation, centrifugation, filtration, diafiltration, ultrafiltration, microfiltration, and settling of solids and removal of supernatant.

The removal of organic solvent, as indicated in step c), can be done according to any of a number of methods known to those of skill in the art including, by way of example and without limitation, evaporation, lyophilization, distillation, desiccation, addition of organic solvent absorbent, liquid/liquid extraction and rotovapping.

The shark material used herein will be a solid and can be, for example, a powder, granulate, rod, or particle. Prior to or during step a), the shark material can be homogenized. As used herein, the terms "homogenize", "homogenizing" and "homogenization" refer to a process of increasing the efficiency of extraction of desired components from cartilage material by either: a) increasing the total or specific surface area of the cartilage material, or b) facilitating the release of desired components from the cartilage material. The homogenization can be conducted by one or more of chemical means, physical means and combinations thereof.

Chemical means for homogenizing the cartilage material will include one or more chemical agents that swell the cartilage material, disrupt or lyse cells or extracellular matrix in the cartilage material, and/or increase the porosity of the cartilage material. Exemplary non-limiting examples of such chemical agents include detergents, surfactants, ionic agents, nonionic agents, reducing agents, chelators, glycosylating agents, chaotropic agents, urea, guanidine, phospholipids, glycolipids, dithiothreitol, β-mercaptoethanol, sodium lauryl sulfate, triton solution and other such agents known to those of skill in the art or disclosed in "A Guide to the Properties and Uses of Detergents in Biology and Biochemistry" by Judith Neugebauer (Calbiochem-Novabiochem Corporation, 1988) the disclosure of which is hereby incorporated by reference.

Physical means for homogenizing the cartilage material will generally result in reducing the average particle size of the shark material thereby increasing its specific surface area. The particle size reduction can be done by any one or more of the following exemplary methods including pulverization, micronization, milling, grinding, chopping, blending under high speed and other methods known to those of skill in the art of particle size reduction.

The extraction solutions can contain extraction enhancing agents which enhance the extraction of components from cartilage. These extraction enhancing agents can include inorganic or organic acids, inorganic or organic bases, polymers, buffers, salts and other similar agents known to those of skill in the art.

According to one embodiment, the extraction of low molecular weight materials from cartilage was done by:

a) treating homogenized shark cartilage material (1 kg) with methanol (1 kg) to form a first mixture comprising soluble components of shark cartilage;

b) centrifuging said first mixture to form a first liquid extract comprising said soluble components and a first mass of solids;

c) evaporating the methanol from said first liquid extract;

d) evaporating a sufficient amount of liquid from said first liquid extract to form a substantially dry second mass of solids;

e) adding water (1 kg) to said second mass of solids to form a second mixture; and f) centrifuging said second mixture to form a first final liquid extract and a third mass of solids.

Steps c) and d) above can be optionally combined to go directly from the first liquid extract to the second mass of solids.

All the liquid extracts resulting from extractions and reiterated extractions of the shark cartilage, from the above steps, were analyzed for their dry weight content and protein concentrations (as determined by a standard Bradford protein assay) as an indication of the recovery of soluble components. The anti-MMP activity was also evaluated. The GIA was conducted on 40 $\mu$l of 20× concentrated samples. The results are summarized in Table 1.

TABLE 1

| Fractions tested | Dry weights (mg/ml) | Protein concentration ($\mu$g/ml) | GIA (% inhibition) |
| --- | --- | --- | --- |
| CTRL-S1 | 21.9 | 2133.8 | 72 |
| CTRL-S2 | 12.1 | 1016.3 | 42 |
| CTRL-S3 | 6.2 | 758.6 | 47 |
| SU-MET-S1 | 14.3 | 54.8 | 52 |
| SU-MET-S2 | 6.1 | 28.6 | 13 |
| SU-MET-S3 | 3.4 | 48.5 | 0 |
| SU-ETH-S1 | 5.5 | 30.8 | 16 |
| SU-ETH-S2 | 7.1 | 79.5 | 4 |
| SU-ETH-S3 | 2.9 | 63.7 | 0 |

As used in Table 1, "CTRL" (control sample) indicates a final liquid extract obtained when using purified water as the extraction solvent. The term "SU-MET" indicates a final liquid extract obtained using methanol as the organic solvent-containing solution. The term "SU-ETH" indicates a final liquid extract obtained using ethanol as the organic solvent-containing solution. The indications "S1", "S2" and "S3" indicate a first final liquid extract, a second final liquid extract, and a third final liquid extract, respectively, using the indicated solvents as the organic solvent-containing solutions or purified water.

The results demonstrate that both aqueous and non-aqueous organic solvent-containing solutions may be used to recover biologically active components exhibiting at least anti-MMP activity from shark cartilage. Moreover, residual activity may be extracted by successive re-extraction of the solid particles of shark cartilage. There is no apparent direct correlation between anti-MMP activity and the amount of material isolated, as determined by dry weight analysis and protein recovery.

Impact Of Cartilage To Purified Water Ratios On The Production Of Liquid Extracts According to a first embodiment of the process of the invention, the crude liquid extract is prepared with water at a cartilage (C) to purified water (E) ratio of about 1 kg to 1 L, respectively. The process for recovering the components comprised the steps of:

a) homogenizing shark cartilage in an aqueous solution until the cartilage is reduced to solid particles having an average particle size of less than about $500\mu$ to form a homogenate;

b) equilibrating said homogenate to extract biologically active components into said aqueous solutions to form a first mixture comprising a first mass of solids and a first liquid extract (LE) containing said biologically active components;

c) separating said first liquid extract from said first mass of solids;

d) subjecting said first liquid extract to a separation procedure to form a second liquid extract containing cartilage molecules having molecular weights less than about 500 kDa (LE-0-500);

e) filtering said second liquid extract through a microfiltration membrane having a nominal porosity of 0.22 microns to form a final liquid extract (P-C1-E1 which is substantially equivalent to the 0-500 fraction);

The present process has also been performed using different cartilage to water ratios as follows:

| Fraction ID | Qty of cartilage (Kg) | Qty of purified water (L) |
|---|---|---|
| *P-C3-E1 | 3 | 1 |
| P-C2-E1 | 2 | 1 |
| P-C1-E1 | 1 | 1 |
| P-C1-E2 | 1 | 2 |
| P-C1-E3 | 1 | 3 |

*P indicates the permeate formed during the separation step.

All the first liquid extracts prepared according to the above procedures were analyzed for their dry weight content, protein concentration and their anti-MMP activity. The results are summarized in Table 2.

TABLE 2

| Fractions tested | Dry weights (mg/ml) | Protein concentration ($\mu$g/ml) | GIA* (% of inhibition) |
|---|---|---|---|
| P-C3-E1 | 25.2 | 482.5 | 55 |
| P-C2-E1 | 22.1 | 379.4 | 52 |
| P-C1-E1 | 15.0 | 324.3 | 54 |
| P-C1-E2 | 9.9 | 191.5 | 32 |
| P-C1-E3 | 6.3 | 157.8 | 24 |

*GIA was performed on 30 $\mu$l aliquots of 20X concentrated samples.

These results indicate that about 20 g of soluble components can be recovered per kilogram of shark cartilage starting material. The maximum recovery of soluble components under the specified conditions were 19.8 (9.9×2) and 18.9 (6.3×3) g of soluble component per kg of shark cartilage (P-C1-E2 and P-C1-E3, respectively).

These results also indicate that the dry weight content, the protein content as well as the components possessing the anti-MMP activity can be efficiently recovered using different cartilage to purified water ratios.

The first solid mass recovered from the P-C1-E1 extraction was re-extracted for 2 more times using the same cartilage to purified water ratio to recover the residual amounts of components contained therein. The process of repeated extraction of the first mass of solids comprises the steps of:

f) treating said first mass of solids recovered from step c) with purified water to form a second mixture which is separated to form a second liquid extract (P-C1-E1-2) and a second mass of solids, wherein said second liquid extract can be treated according to steps d) and e); and, optionally g) repeating step f) with said second mass of solids to form a third liquid extract (P-C1-E1-3) and a third mass of solids, wherein said third liquid extract can be treated according to steps d) and e).

Table 3 summarizes the amount of water and shark cartilage used in steps a) through g) above.

TABLE 3

| Fraction ID | Qty of Cartilage (Kg) | Qty of purified water (L) |
|---|---|---|
| P-C1-E1 | 1 | 1 |
| P-C1-E1-2 | mass of solids after recovery of P-C1-E1 | 1 |
| P-C1-E1-3 | mass of solids after recovery of P-C1-E1-2 | 1 |

All the liquid extracts resulting from the above procedure were analyzed for dry weight content, protein concentration and anti-MMP activity. The results are summarized in Table 4.

TABLE 4

| Fractions tested | Dry weights (mg/ml) | Protein concentration ($\mu$g/ml) | GIA* (% of inhibition) |
|---|---|---|---|
| P-C1-E1 | 15.0 | 324.3 | 54 |
| P-C1-E1-2 | 4.3 | 54.5 | 21 |
| P-C1-E1-3 | 1.3 | 27.0 | 17 |

*GIA was conducted on 30 $\mu$l aliquots of 20X concentrated samples.

These results indicate that one or more extractions of shark cartilage according to steps a) through c) above can result in increased recovery of the soluble components of the shark cartilage. Moreover, residual amounts of components possessing anti-MMP activity can still be extracted after a second and third extraction of the same solid particles.

It will be apparent to those of skill in the art that modifications to the extraction parameters such as the temperature, the number of extractions or the extracting solvent, for example, can be made to optimize the amounts of recovered solids, protein and biologically active components.

A process for preparing Various Molecular Weight Fractions of Components Derived from Cartilage The 0-500 fraction: The 0-500 fraction is a shark cartilage liquid extract comprising components having molecular weights less than about 500 kDa. Preparative methods for the 0-500 fraction are disclosed in International Publication No. WO 95/32722, WO 96/23512, and WO 97/16197, the relevant disclosures of which are hereby incorporated by reference. These prior art methods comprise the steps of:

a) homogenizing shark cartilage in an aqueous solution in conditions compatible with the preservation of the integrity of biologically active components present in cartilage until the cartilage is reduced to solid particles whose size is less than about 500 μm;

b) extracting said biological active components into said aqueous solution, which results in a mixture of solid particles and of crude liquid extract (LE) having said biologically active components;

c) separating said liquid extract from said solid particles;

d) further separating the crude liquid extract so as to obtain a final liquid extract containing molecules having molecular weights less than about 500 kDa (LE-0-500); and e) filtering the LE-0-500 on a microfiltration membrane (0.22 micron) and freezing to obtain the final liquid extract (0-500 fraction).

The 0-1 and 1-500 fractions: The 0-1 fraction is a shark cartilage liquid extract comprising components having molecular weights less than about 1 kDa. The 1-500 fraction is a shark cartilage liquid extract comprising components having molecular weights between about 1–500 kDa. The 0-1 and 1-500 fractions of shark cartilage extract were prepared with an ultrafiltration system using a membrane having a nominal molecular weight cut-off of about 1 kDa. Using this system, the two cartilage fractions were obtained after one cycle of purification (one cycle of purification being defined by the arrest of the purification step when 50% of the permeate is recovered). The 1-500 fraction comprised the retentate (R) which, when reconstituted using purified water in a final volume equivalent to the original volume of the cartilage extract used for the purification, comprises components having molecular weights of about 1 to 500 kDa at a 1× concentration and components having molecular weights less than about 1 kDa at a 0.5× concentration with regard to the original extract used for the purification. The 0-1 fraction comprised the permeate (P) which is composed only of components having molecular weights less than about 1 kDa at a 1× concentration. Using the ultrafiltration system, the 1-500 fraction was further purified by additional purification cycles as demonstrated in Table 5.

TABLE 5

THEORETICAL CONCENTRATION AFTER SUCCESSIVE ULTRAFILTRATION ON A PM1

| CYCLE OF PURIFI-CATION | PERMEATE (P) | | RETENTATE (R) | | |
|---|---|---|---|---|---|
| | Fraction ID | [<1 KDa] | Fraction ID | [<1 KDa] | [1-500 KDa] |
| 1 | P1-0-1 | 1× | R1-1-500 | 0.5× | 1× |
| 2 | P2-0-1 | 0.5× | R2-1-500 | 0.25× | 1× |
| 3 | P3-0-1 | 0.25 | R3-1-500 | 0.13× | 1× |
| 4 | P4-0-1 | 0.13× | R4-1-500 | 0.06× | 1× |
| 5 | P5-0-1 | 0.06× | R5-1-500 | 0.03× | 1× |
| 6 | P6-0-1 | 0.03× | R6-1-500 | 0.02× | 1× |

Multiple batches of the 0-1 and 1-500 fractions were prepared according to the above procedures. In order to minimize the formation of aggregates and to improve the dissolution and the maintenance of a, stable, soluble form, a 1% w/v sucrose aqueous solution was used as a stabilizer for extraction The 0-1 and 1-500 fractions were obtained by first preparing a batch of the LE-0-500 fraction according to the prior art methods described above and second adding the following novel steps:

e) optionally preparing the LE-0-500 extract with a solution containing sucrose to a final concentration of about 1% (w/v) to form the LE-0-500 fraction with 1% sucrose;

f) filtering the LE-0-500 or LE-0-500 with 1% sucrose with a membrane having a nominal molecular weight cut-off of about 1 kDa to form liquid extracts comprising cartilage molecules having molecular weights less than about 1 kDa (Pn-0-1 and fraction Pn-0-1 with 1% sucrose, respectively, wherein "n" indicates the purification cycle in Table 5), and to form retentate liquid extracts (Rn-0-1 and fraction Rn-0-1 with 1% sucrose, respectively, wherein "n" indicates the purification cycle in Table 5) comprising cartilage molecules having molecular weights greater than about 1 kDa; and;

g) microfiltering the retentate and permeate liquid extracts through a microfiltration membrane having a porosity of about 0.22 microns.

The above procedure can be performed without including step e) so as to prepare extracts that are free of sucrose. The retentate liquid extracts can be ultrafiltered for one or more, preferably four or more, cycles of purification to form additional filtrate liquid extracts comprising cartilage components having molecular weights less than about 1 kDa (P1-0-1 through P6-0-1) and to form retentate extracts comprising cartilage components having molecular weights between 1 to about 500 kDa (R6-1-500 and R6-1-500 with 1% sucrose). The liquid extracts can optionally be frozen for storage.

Accordingly, the procedure just described was used to prepare the following liquid extracts.

1) 0-500 fraction prepared from LE 0-500
2) 0-500 fraction with 1% sucrose prepared from LE-0-500 with 1% sucrose
3) 0-1 fraction prepared from P1-0-1
4) 0-1 fraction with 1% sucrose prepared form P1-0-1 with 1% sucrose
5) 1-500 fraction prepared from R6-1-500
6) 1-500 fraction with 1% sucrose prepared from R6-1-500 with 1% sucrose.

The second mass of solids obtained from the separation of the second mixture which was formed during the treatment of the first mass of solids with water can be repeatedly extracted with water to recover additional amounts of the soluble fraction of shark cartilage.

All liquid extracts prepared according to the above procedure were analyzed for their dry weight and protein content. In addition, the anti-MMP activity as well as the antiangiogenic and the anti-tumor activities of each fraction were also determined. The results are summarized in Table 6.

TABLE 6

| FRAC-TIONS TESTED | DRY WEIGHTS (mg/ml) | PROTEIN CONCEN-TRATION (μg/ml) | GIA* (% of inhi-bition) | EVT (% of ef-ficacy) | LLC (% of ef-ficacy) |
|---|---|---|---|---|---|
| Saline | — | — | — | — | 0 |
| 0-500 fraction | 14.8 | 256.1 | 49 | 100 | 32.9 |
| 0-1 fraction | 12.1 | 0.0 | 26 | 80 | 31.0 |
| 1-500 fraction | 0.2 | 163.9 | 21 | 0 | 20.5 |
| 0-500 fraction in 1% sucrose | 24.7 | 274.5 | 59 | 75 | 42.5 |

TABLE 6-continued

| FRAC-TIONS TESTED | DRY WEIGHTS (mg/ml) | PROTEIN CONCEN-TRATION (μg/ml) | GIA* (% of inhi-bition) | EVT (% of ef-ficacy) | LLC (% of ef-ficacy) |
|---|---|---|---|---|---|
| 0-1 fraction in 1% sucrose | 20.3 | 0 | 29 | 100 | 29.2 |
| 1-500 fraction in 1% sucrose | 11.1 | 212.6 | 14 | 20 | 32.8 |

*GIA was performed on 30 μl aliquots of 20× concentrated samples.

The analytical results demonstrate that both the 0-1 fraction and the same with 1% sucrose, while containing over 90% of the recovered dry weight content, comprise very low amounts, almost undetectable amounts, of proteins.

However, anti-MMP activity was observed in both the 0-1 fraction as well as the 1-500 fraction suggesting that 1) at least one non-protein component is responsible for this activity, and 2) more than one component may have anti-MMP activity. The active component may or may not be of a protein or peptide nature.

Further, the antiangiogenic activity, as measured according to the EVT, was observed exclusively in the 0-1 fraction. We note that the presence of sucrose was responsible for a slight recovery of antiangiogenic activity in the 1-500 fraction in 1% sucrose.

Treatment of animals, inoculated with M27 tumor cells (LLC), resulted in a significant reduction in the number of macroscopically visible metastatic nodules at the surface of the lung. Both the 0-1 and 0-500 fractions induced a significant reduction in the number of metastatic nodules (about 30%). However, the 1-500 fraction was less active than either the 0-1 or 0-500 fractions suggesting that an active component in the 0-1 fraction is at least partly responsible for the anti-tumor activity. These results also suggest the presence of another anti-tumor component in the 1-500 fraction. Some additional groups of animals have been treated with the same molecular weights fractions containing 1% w/v sucrose. Although the present inventors did not observe any significant difference between groups, there is however a trend for high molecular weights fractions to be more active in the presence of sucrose (above Table). The present inventors did not observe any decrease of animals body weights suggesting the absence of toxicity of the cartilage extract in the LLC model.

Isolation and Characterization of an Anti-MMP Component

Chromatographic Isolation and Purification

Having found that a plurality of components possessing useful biological activities are present in the 0-500 fraction and more specifically in the 0-1 fraction, the next step was to isolate active components therefrom.

Four different procedures were developed to isolate and purify components containing anti-MMP activity from the 0-500 fraction.

Procedure 1

Step 1

The 0-500 fraction obtained by the above detailed procedure was lyophilized and reconstituted (to a 20-fold concentration with regard to the original volume) in purified water. The reconstituted material was sonicated for 15 minutes to optimize solubilization of biologically active components. After a separation procedure, such as centrifugation at 2200 g for 10 min at 4° C., the supernatant was kept for further purification.

Step 2

Adsorptive chromatography using a solid phase extraction column (SPE-C18 neutral) was performed.

An SPE column packed with 500 mg of C18 sorbent (Supelco No. 5-7012, dimension 3 cc) was conditioned two times in 2 ml of methanol (100%) and three times in 2 ml of purified water. One ml of the 20× reconstituted cartilage extract was loaded onto the column. The sorbent bead was washed with 1.5 ml of purified water, and the components possessing anti-MMP activity were eluted with two 2.5 ml portions of purified water which were combined to form a first eluant.

About 50% of the anti-MMP initial activity was recovered in the first eluant. The remaining 50% was lost during the column loading and washing steps. Neutral conditions therefore appeared to provide weak retention of components possessing the anti-MMP activity. Weak retention of the components, while using this chromatographic medium, is indicative of polar or ionic components.

Step 3

After repeating the above process a plurality of times with various samples of 20× reconstituted cartilage extract, the respective first eluants were pooled and evaporated on a Speed Vac centrifuge. The solids obtained therefrom were reconstituted in purified water at a 200-fold concentration with regard to the original volume of the 0-500 fraction used. After sonication and centrifugation, the supernatant was kept for the next step of purification.

Step 4

A low resolution semi-preparative HPLC separation of the biologically active components present in the supernatant was performed in neutral conditions. A Novapack C18HR (7.6×300 mm; Waters) column was used. The mobile phase used was sodium phosphate (0.01 M pH 7)/methanol (92:8). The flow rate and temperature were maintained at 2 ml/minute and 30° C., respectively. The above 200× reconstituted fraction (100 μl) was injected onto the column and 2 ml fractions were collected using isocratic elution conditions and UV detection (205 nm). The running time was 30 minutes. Components possessing anti-MMP activity were found in eluant fractions corresponding to those having a retention time between 11 and 13 minutes.

Step 5

Step 4 was repeated with various 100 μl aliquots of the 200×reconstituted fraction and the corresponding desired eluant fractions pooled, evaporated, reconstituted in purified water, at a 500× concentration with regard to the original volume of the 0-500 fraction used, and sonicated and centrifuged. The supernatant was kept for the next step of purification.

Step 6

A higher resolution semi-preparative HPLC in neutral conditions was performed on the supernatant obtained from Step 5. The procedure used for this higher resolution semi-preparative HPLC resembles that of step 4 above except that the phosphate buffer (0.01 M, pH 7)/methanol (97:3) is used as the mobile phase. Components possessing anti-MMP activity were found in eluant fractions corresponding to those having a retention time between 23 and 27 minutes.

Step 7

After repeating step 6, pooling the corresponding eluant fractions containing active components and evaporating the solvent to form a substantially solid residue, the residue was reconstituted in water, at a 500–2000×concentration with regard to the original volume of the 0-500 fraction used, and sonicated and centrifuged and kept for further molecular weight analysis and determination of its anti-MMP activity. The biologically active component was termed "Æ-986".

Procedure 2

It was determined that generally a better retention of Æ-986 on the C18 phase chromatography medium was observed at pH 3. Therefore, the SPE procedure (step 2 above) as well as the semi-preparative chromatographic system (steps 4 and 6 above) were modified. The conditions below allow the use of a stronger washing solution in the SPE procedure resulting in a cleaner final extract and in the elimination of one of the semi-preparative purification steps (step 4 of procedure 1).

For example, steps 1 to 3 of procedure 1 were repeated. Step 4 was replaced by the following:

Step 4

The same SPE C-18 column as in step 2 above was used, but the chromatographic medium was conditioned three times with 2 ml of ammonium formate (0.01M, pH 3). One ml of 200×reconstituted extract, obtained from step 3 (pH adjusted to 3 with formic acid prior loading of the samples), was loaded onto the column. The sorbent bed was washed three times with 2 ml ammonium formate/methanol (90:10, at pH 3). Elution of the Æ-986 was performed with 1 ml of methanol (100%). It will be apparent to those of skill in the art that fractions obtained from methanolic elution of the column will contain water. Consequently, the eluting solvent in this step can be another organic solvent, preferably a polar and/or water miscible organic solvent, and the eluting solvent can contain water.

Step 5

Step 5 of procedure 1 was repeated, except that the concentration of the reconstituted anti-MMP fraction was 4000×.

Step 6

This step is identical to step 6 of procedure 1, except that the mobile phase was ammonium formate/methanol (75:25 pH 3).

Step 7

Step 7 was the same as step 7 of procedure 1 except that the same concentration of 4000×was kept as described in the preceding step 6.

Procedure 3

This procedure is substantially the same as procedure 2, except that in step 6 the pH of the formate buffer was changed from acidic (pH 3) to neutral conditions (about pH 7).

Procedure 4

In this purification procedure, an acidic mobile phase was used from the beginning.

Step 1

The pH of the original 0-500 fraction (at a 1× concentration) was adjusted to pH 3 with formic acid and then centrifuged for 10 minutes at 2200 g. The supernatant as used in step 2.

Step 2

The supernatant was loaded onto an SPE C-18 cartridge (Supelco #5.-7136: dimension 60 cc packed with 10 g of solid phase support) that had been conditioned under acidic conditions. The column was conditioned with 120 ml methanol (100%) and 120 ml formic acid (0.01 M, pH 3). Five hundred ml of 1× acidified cartilage extract was loaded onto the column and eluted with six volumes of 100 ml of formic acid (0.01M (pH 3)/methanol 90:10). Biologically active components were obtained in eluant fractions 3, 4, and 5.

Step 3

The eluant fractions 3, 4 and 5 of step 2 were pooled and the solvent evaporated to near dryness. The fractions were then diluted to a concentration of 4000×of original to form an Æ-986 containing solution.

Step 4

The Æ-986 was purified on a preparative HPLC column in formic acid buffer pH 3. The column (Prodigy OSD-prep, 10u, 250×50 mm, from Phenomenex) was conditioned and run at room temperature. The composition of the mobile phase was formic acid (0.01 M, pH 3)/methanol (70:30) and the flow rate was 45 ml/min. Four ml of the SPE C-18 fraction at 4000×concentration were injected onto and eluted from the column in an isocratic mode using UV detection (205 nm). Fractions were collected in one minute intervals for 60 minutes. The anti-MMP activity of the Æ-986 was eluted between 33 and 36 minutes.

Step 5

The fractions exhibiting anti-MMP activity were pooled and evaporated to obtain a 10000×concentrated fraction.

Step 6

This step is identical to step 6 of procedure 2 except that the mobile phase was formic acid (0.01 M, pH 3)/methanol (75:25). Five hundred $\mu$l aliquots of the 10000× concentrated fraction were loaded onto the column. Components containing anti-MMP activity were eluted between 21 and 23 minutes.

Step 7

Step 7 was the same as the step 7 of procedure 1. The same concentration 4000× was preserved as in the preceding step 6.

Semi-purified fractions prepared according to Procedure 1: The present inventors show for the first time that an HPLC-purified fraction (the fraction resulting from procedure 1 described above) has components possessing an anti-MMP activity. The components thus purified also show anti-tumor activity as demonstrated in the in vivo model LLC described above. The anti-tumor activity was determined by treating animals with 3 different concentrations of the HPLC-purified fraction. A bell-shape dose response curve with a maximum efficacy of about 50% (p<0.005) for the 2.5× concentration dose (the concentration being based in a 100% recovery during the purification steps and with regard to the original volume of cartilage extract) was observed.

Since angiogenesis and matrix metalloprotease activity are closely linked to tumor proliferation and metastasis progression, the HPLC purified fraction representing an anti-MMP component may be responsible for the anti-tumor activity. Therefore, components possessing these activities are potential therapeutic agents in the treatment of cancer (Tolnay, E. et al., *J. Cancer Res Clin. Oncol.* 123: 652–658, 1997; Skobe, M., et al. *Nature Medicine,* 3: 1222–1227, 1997).

Semi-purified fractions prepared according to Procedure 4: The fractions in this section were prepared according to procedure 4 above except that steps 2) and 3) were conducted as follows.

Step 2

The supernatant was loaded onto an SPE C-18 cartridge (Supelco #5.-7012: dimension 3 cc packed with 500 mg of solid phase support) that had been conditioned under acidic conditions. The column was conditioned with 4 ml methanol (100%) and 6 ml formic acid (0.01 M, pH 3). Ten ml of 1× acidified cartilage extract was loaded onto the column washed three times with 1.0 mL volumes of formic acid (0.01M (pH 3)/methanol 90:10) and the biologically active components eluted therefrom with 1.0 mL of methanol.

Step 3:

The eluant fraction of step 2 containing biologically active components was evaporated to dryness. The fractions were then diluted to a concentration of 40× or 20× of original to form an Æ-986 containing solution.

All the liquid extracts resulting from this procedure were analyzed for anti-MMP activity. The results are summarized in Table 7.

TABLE 7

| Fractions tested | GIA (% of inhibition) |
| --- | --- |
| CTRL-S1* | 57 |
| CTRL-S2* | 16 |
| CTRL-S3* | 4 |
| SU-MET-S1* | 55 |
| SU-MET-S2* | 15 |
| SU-MET-S3* | 0 |
| SU-ETH-S1* | 14 |
| SU-ETH-S2* | 1 |
| SU-ETH-S3* | 0 |
| 0-500 fraction** | 64 |
| 0-1 fraction** | 56 |
| 1-500 fraction** | 16 |
| 0-500 fraction in 1% sucrose** | 74 |
| 0-1 fraction in 1% sucrose** | 40 |
| 1-500 fraction in 1% sucrose** | 16 |
| P-C3-E1* | 57 |
| P-C2-E1* | 60 |
| P-C1-E1* | 46 |
| P-C1-E2* | 39 |
| P-C3-E3* | 17 |
| P-C1-E1-2* | 16 |
| P-C1-E1-3* | 4 |

*GIA was performed on 80 µl aliquots of 20X concentrated samples.
**GIA was performed on 80 µl aliquots of 40X concentrated samples.

Thus, the process of the present invention provides for the preparation of specific shark cartilage fractions possessing anti-MMP activity. Further, both aqueous and organic solvent-containing solutions can be used to prepare cartilage extracts possessing at least an anti-MMP activity. Although both of the 0-500 and 1-500 fractions have anti-MMP activity, anti-MMP components purified by the present procedure are mainly contained within the 0–1 kDa portion. Similar results have been observed in the equivalent fractions containing 1% w/v sucrose. Finally, the anti-MMP activity can be efficiently recovered using different cartilage to purified water ratios.

Molecular Weight Determination of the Anti-MMP Component by LC/MS

Five multi-dimensional chromatographic systems were developed to facilitate the determination of molecular weight of shark cartilage fractions by liquid chromatography/mass spectrometry (LC/MS). Each of five systems is presented below in Tables 8–12.

The experiments involve MS Scanning of the split (7:1) chromatographic column eluant as well as fraction collection from the LC to be used for post-run anti-MMP activity determinations. This association between MS and anti-MMP biological activity specifically identifies the elution fraction as well as the retention time of the compound of interest for each of the chromatographic system used.

For MS negative ions detection, a solution of ammonium hydroxide (0.75% v/v at 0.15 ml/min.) was added to the column eluant prior to introduction into the MS ion source. The resulting pH of the mixture was between 8 to 10 which improve MS negative ions formation and detection.

TABLE 8

CHROMATOGRAPHIC SYSTEM 1: Isocratic C18 neutral condition (ammonium formate)

| Column | C18 ODS-2, 5u, 4.6 × 250 mm, Phenomenex |
| --- | --- |
| Column temperature | 30° C. |
| Flow rate | 0.7 ml/min. |
| Injection volume | 100 µl of purified fraction |
| Eluant | Ammonium formate (0.01 M, pH 7)/methanol (96:4) |
| Elution mode | Isocratic |
| Detection | UV: 205 nm, 254 nm, MS |
| Run time | 25 min. |
| Fraction collection | each min. or 30 sec. with different delay time. |

Anti-MMP activity of the collected fractions was evaluated.

TABLE 9

CHROMATOGRAPHIC SYSTEM 2: Gradient C18 acid condition (ammonium formate)

| Column | C18 ODS-2, 5u, 4.6 × 250 mm, Phenomenex | | |
| --- | --- | --- | --- |
| Column temperature | 30° C. | | |
| Flow rate | 0.7 ml/min. | | |
| Injection volume | 100 µl of purified fraction | | |
| Eluant A | Ammonium formate (0.01 M, pH 3)/methanol (96:4) | | |
| Eluant B | Methanol | | |
| Gradient | Time | Eluant A | Eluant B |
| | 0 | 100 | 0 |
| | 2 | 100 | 0 |
| | 22 | 20 | 80 |
| | 25 | 20 | 80 |
| Detection | UV: 205 nm, 254 nm, MS | | |
| Run time | 25 min. | | |
| Fraction collection | each min. or 30 sec. with different delay time. | | |

Anti-MMP activity of the collected fractions was evaluated.

TABLE 10

CHROMATOGRAPHIC SYSTEM 3: Isocratic C18 acid condition (ammonium formate)

| Column | C18 ODS-2, 5u, 4.6 × 250 mm, Phenomenex |
| --- | --- |
| Column temperature | 30° C. |
| Flow rate | 0.7 ml/min. |
| Injection volume | 100 µl of purified fraction |
| Eluant | Ammonium formate (0.01 M, pH 3)/methanol (75:25) |
| Elution mode | Isocratic |
| Detection | UV: 205 nm, 254 nm, MS |
| Run time | 25 min. |
| Fraction collection | each min. or 30 sec. with different delay time. |

Anti-MMP activity of the collected fractions was evaluated.

TABLE 11

CHROMATOGRAPHIC SYSTEM 4: Gradient $NH_2$ acid condition (ammonium formate)

| Column | $NH_2$, 5u, 3.6 × 250 mm, Phenomenex | | |
| --- | --- | --- | --- |
| Column temperature | 30° C. | | |
| Flow rate | 0.7 ml/min. | | |
| Injection volume | 100 µl of purified fraction | | |
| Eluant A | Ammonium formate (0.01 M, pH 3)/methanol (96:4) | | |
| Eluant B | Methanol | | |
| Gradient | Time | Eluant A | Eluant B |
| | 0 | 100 | 0 |
| | 2 | 100 | 0 |
| | 22 | 20 | 80 |
| | 25 | 20 | 80 |

TABLE 11-continued

CHROMATOGRAPHIC SYSTEM 4: Gradient NH$_2$ acid condition (ammonium formate)

| | |
|---|---|
| Detection | UV: 205 nm, 254 nm, MS |
| Run time | 25 min. |
| Fraction collection | each min. or 30 sec. with different delay time. |

Anti-MMP activity of the collected fractions was evaluated.

TABLE 12

CHROMATOGRAPHIC SYSTEM 5: Isocratic C18 acid condition (ammonium acetate)

| | |
|---|---|
| Column | C18 ODS-2, 5u, 4.6 × 250 mm, Phenomenex |
| Column temperature | 30° C. |
| Flow rate | 0.7 ml/min. |
| Injection volume | 100 μl of purified fraction |
| Eluant | Ammonium formate (0.01 M, pH 3)/ methanol (75:25) |
| Elution mode | Isocratic |
| Detection | UV: 205 mn, 254 mn, MS |
| Run time | 25 min. |
| Fraction collection | each min. or 30 sec. with different delay time. |

Anti-MMP activity of the collected fractions was evaluated.

The multidimensional chromatographic experiments were conducted by injecting 100 μl of 500 to 1000× of the purified phosphate final fraction (obtained from step 7 of purification procedure 1). At this concentration, no strong and clear signal of the Æ-986 was detected in the MS scan mode (total ions). Peaks of interest were detected by post run monitoring all the individual ion signal (100–1000 amu) in the region of interest (active fractions).

Injection of purified fractions with concentrations of up to 2000× showed a small peak in the total ion chromatogram as well as in the base peak chromatogram corresponding to the Æ-986.

In positive ion detection mode (Table 13) only ions 245 M+1 and 227 were clearly detected in the region of interest (Æ-986). As per the design and the operation in the LCQ MS, the observation of ions corresponding to the loss of a molecule of water as well as the molecular ion (M+1) is usual and frequent for an analyte containing an alcohol functional group. The co-elution profile of the ions 245 M+1 and 227 as well as the 18 amu difference corresponding to the loss of a molecule of water (H$_2$O), strongly suggest the presence of a single component of interest with a molecular weight of 244, 245 being equivalent to the M+1 species in positive ion mode.

Examples of total ion chromatogram (TIC) as well as the single ion chromatogram (245 M+1 m/e) obtained from the injection of the semi-purified Æ-986 on different chromatographic system are presented in FIGS. 1 to 4. The post-run analysis of those chromatograms indicated the presence of the ion 245 (M+1) in each of the fractions collected from the different chromatographic systems which contain components possessing anti-MMP activity.

Figure 1B:
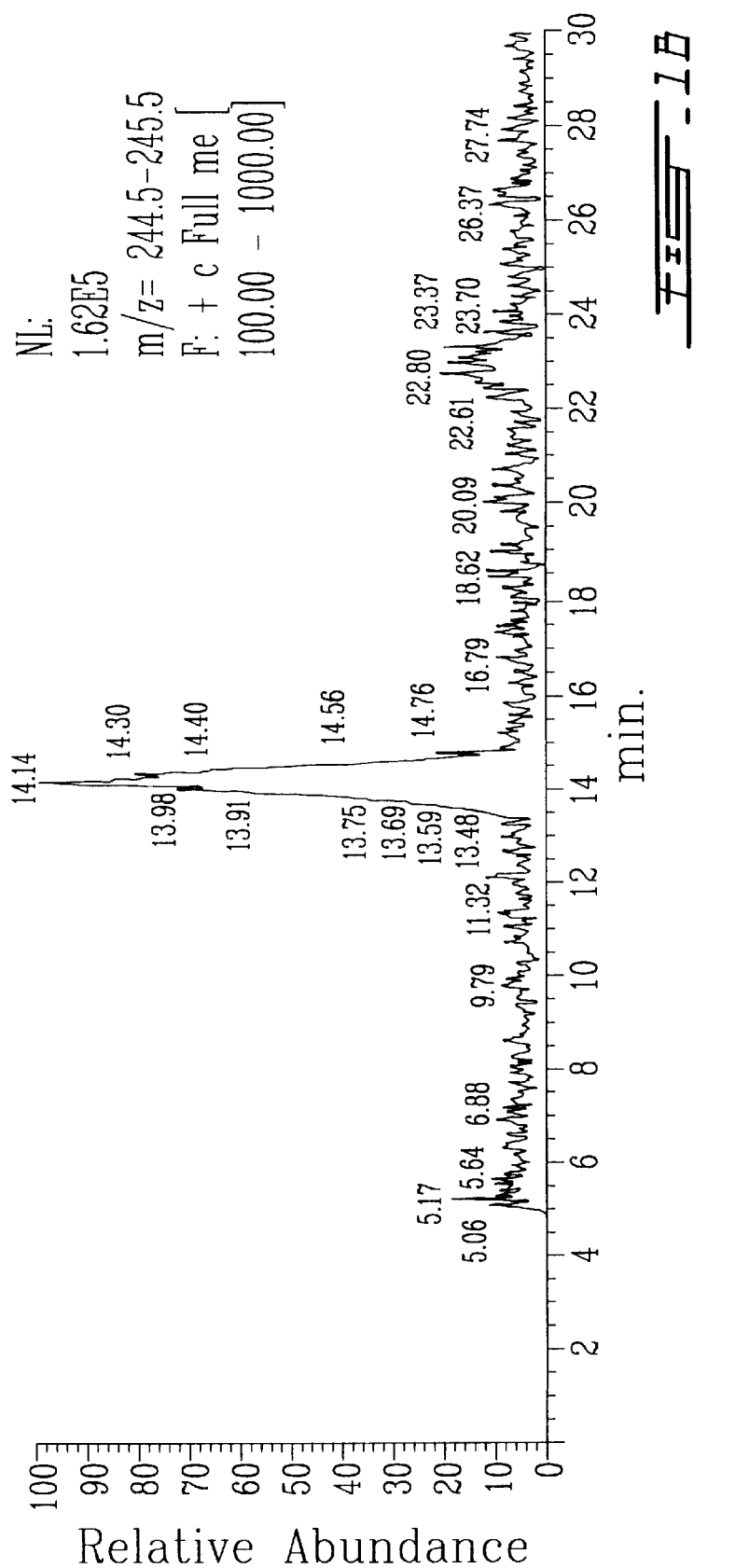

The total ion chromatogram as well as the single ion chromatogram (245 M+1) obtained from analysis of the Æ-986 isolated on the HPLC C18 system (ammonium formate neutral pH 7 isocratic) are presented in FIG. 1. The Æ-986 was detected in fractions collected between 13.5 to 15.0 minutes corresponding to a 14.14 minutes retention time for elution of the m/e 245 M+1 peak.

Figure 2A:
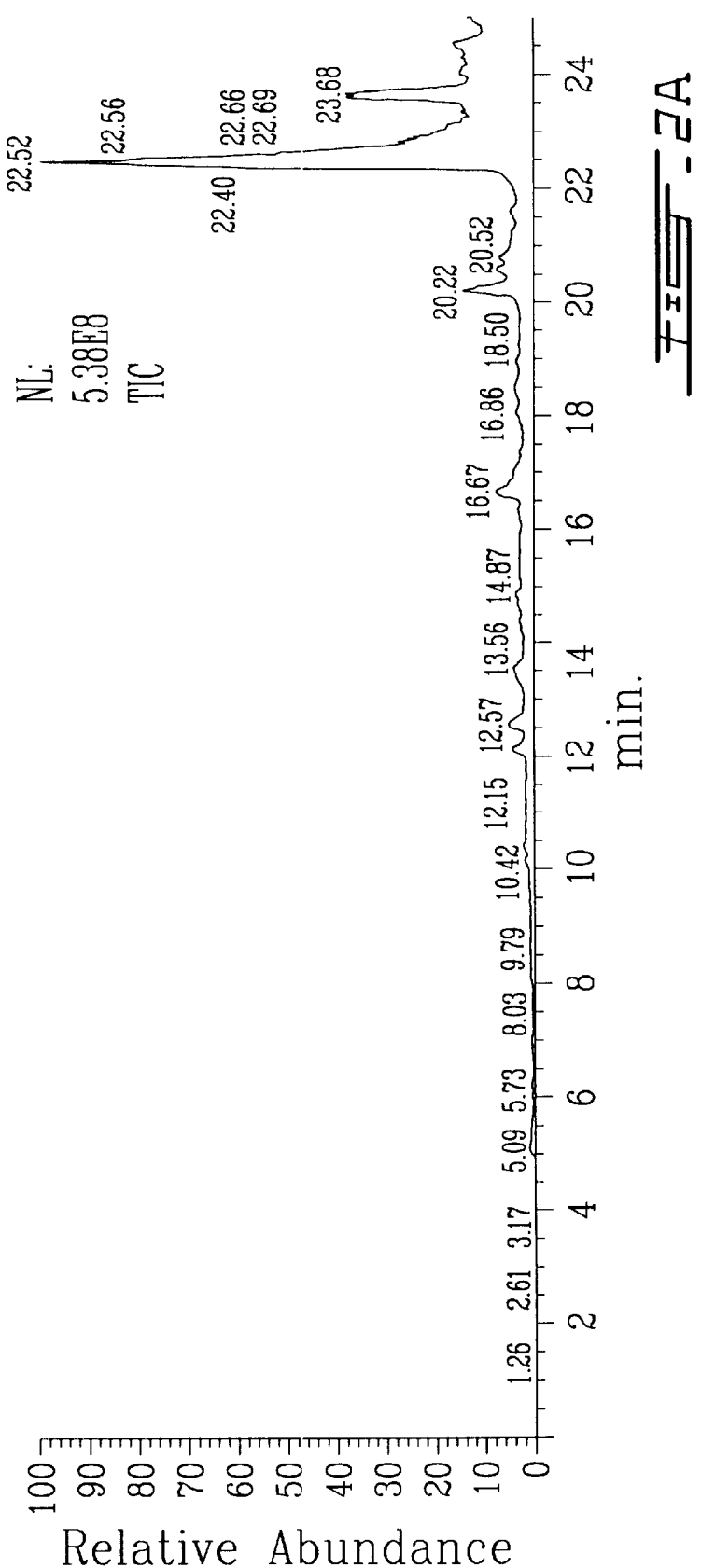

The total ion chromatogram as well as the single ion chromatogram (245 M+1) obtained from analysis of the Æ-986 isolated on the HPLC C18 system (ammonium formate acid pH 3 gradient) are presented in FIG. 2. The Æ-986 was detected in fractions collected between 16.5 to 17.0 minutes corresponding to a 16.62 minutes retention time for elution of the m/e 245 M+1 peak.

Figure 3A:
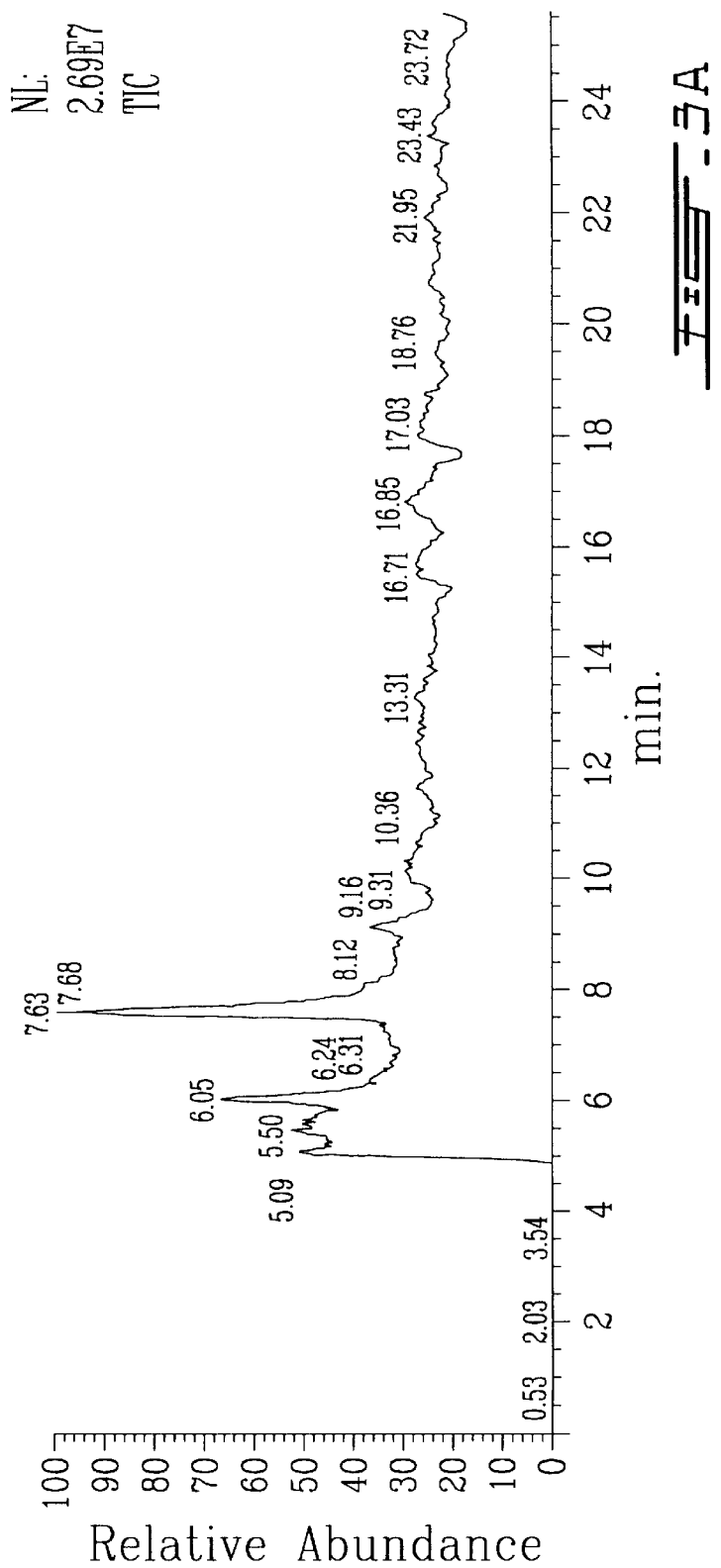
FIGS. 3a and 3b depict the total ion chromatogram as well as the single ion chromatogram (245) obtained from analysis of the Æ-986 on an HPLC C18 system using an ammonium formate buffer (pH 3) and isocratic elution.
Figure 3B:
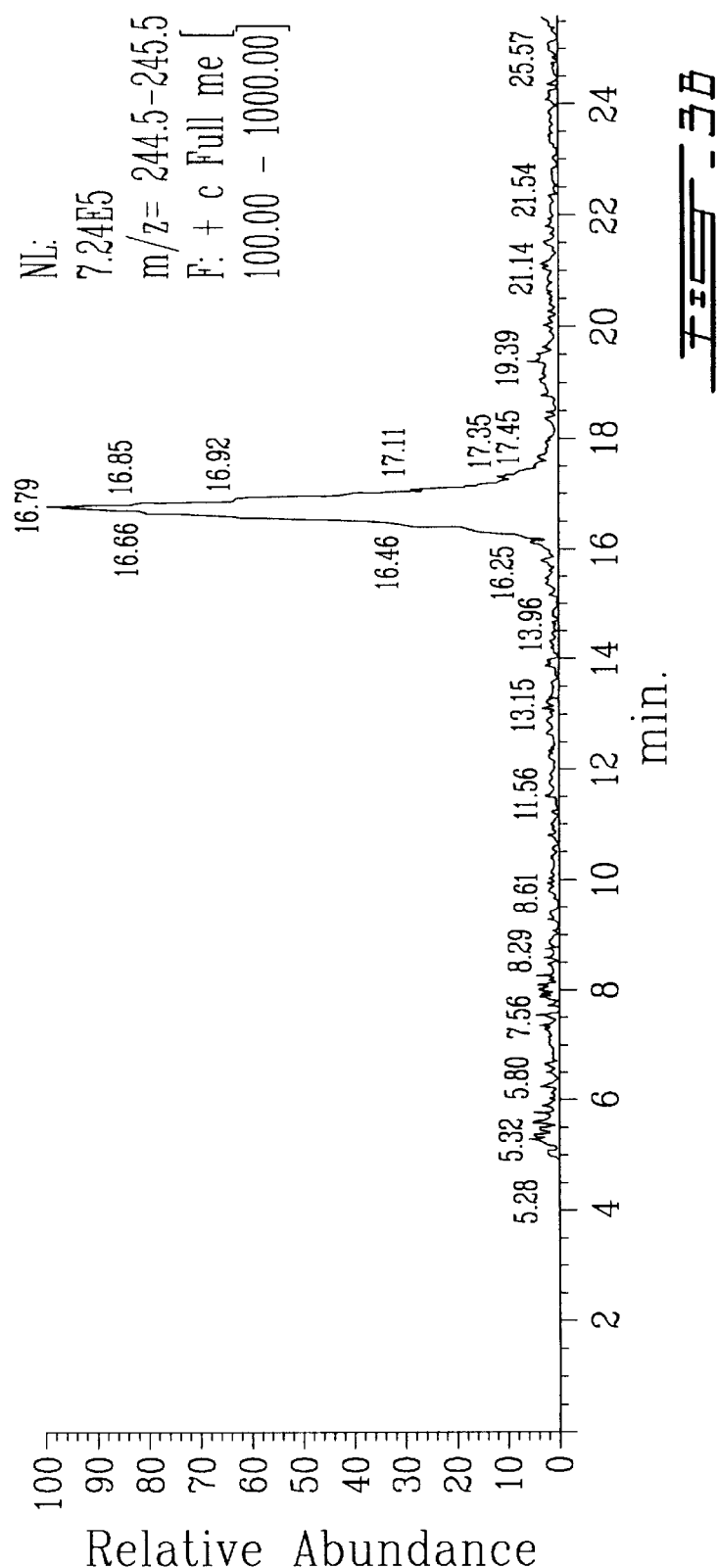

The total ion chromatogram as well as the single ion chromatogram (245) obtained from analysis of the Æ-986 isolated on the HPLC C18 system (ammonium formate acid pH 3 isocratic) are presented in FIG. 3. The Æ-986 was detected in fractions collected between 16 to 18 minutes corresponding to a 16.79 minutes retention time for elution of the m/e 245 M+1 peak.

Figure 4A:
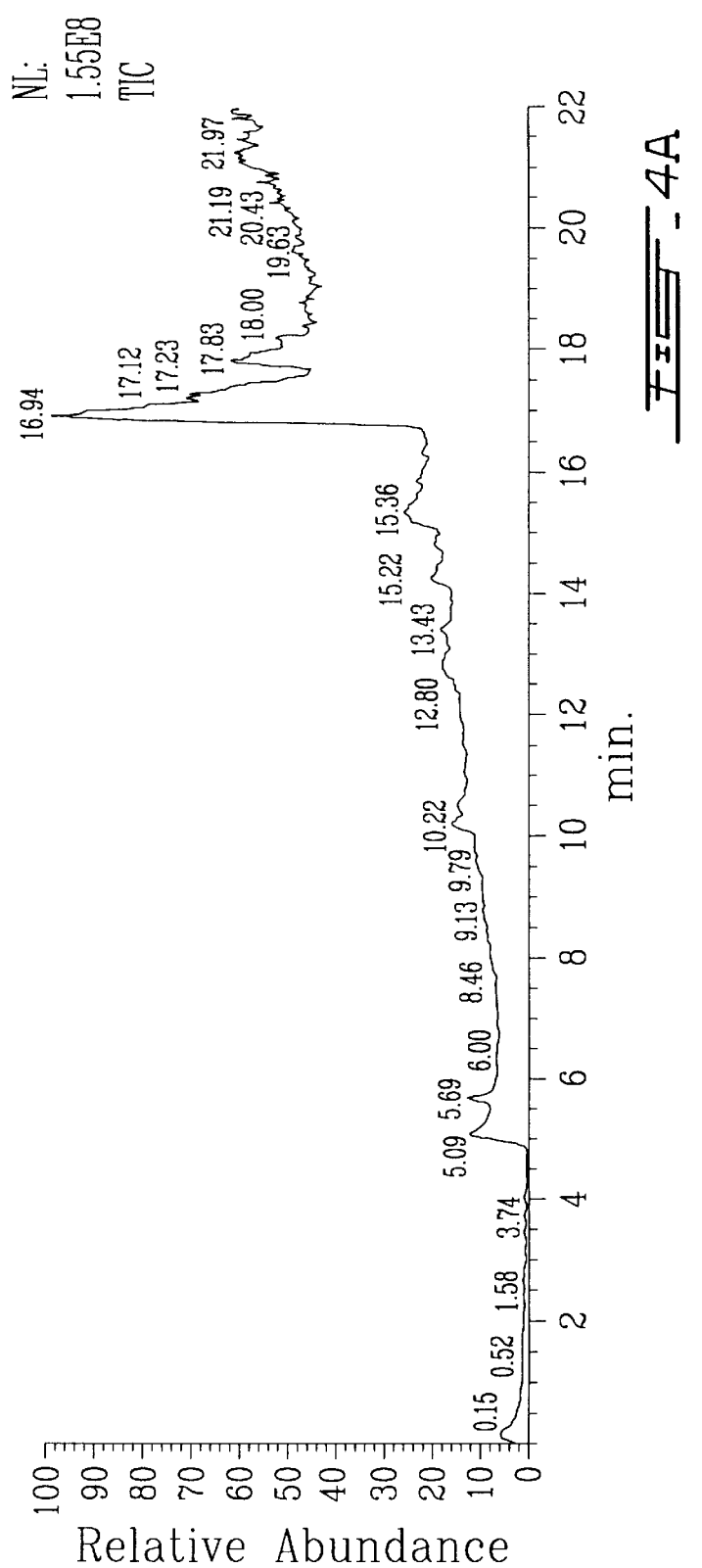
FIGS. 4a and 4b depict the total ion chromatogram as well as the single chromatogram (245) obtained from analysis of the Æ-986 on an HPLC NH2 system using an ammonium formate buffer (pH 3) and gradient elution.
Figure 4B:
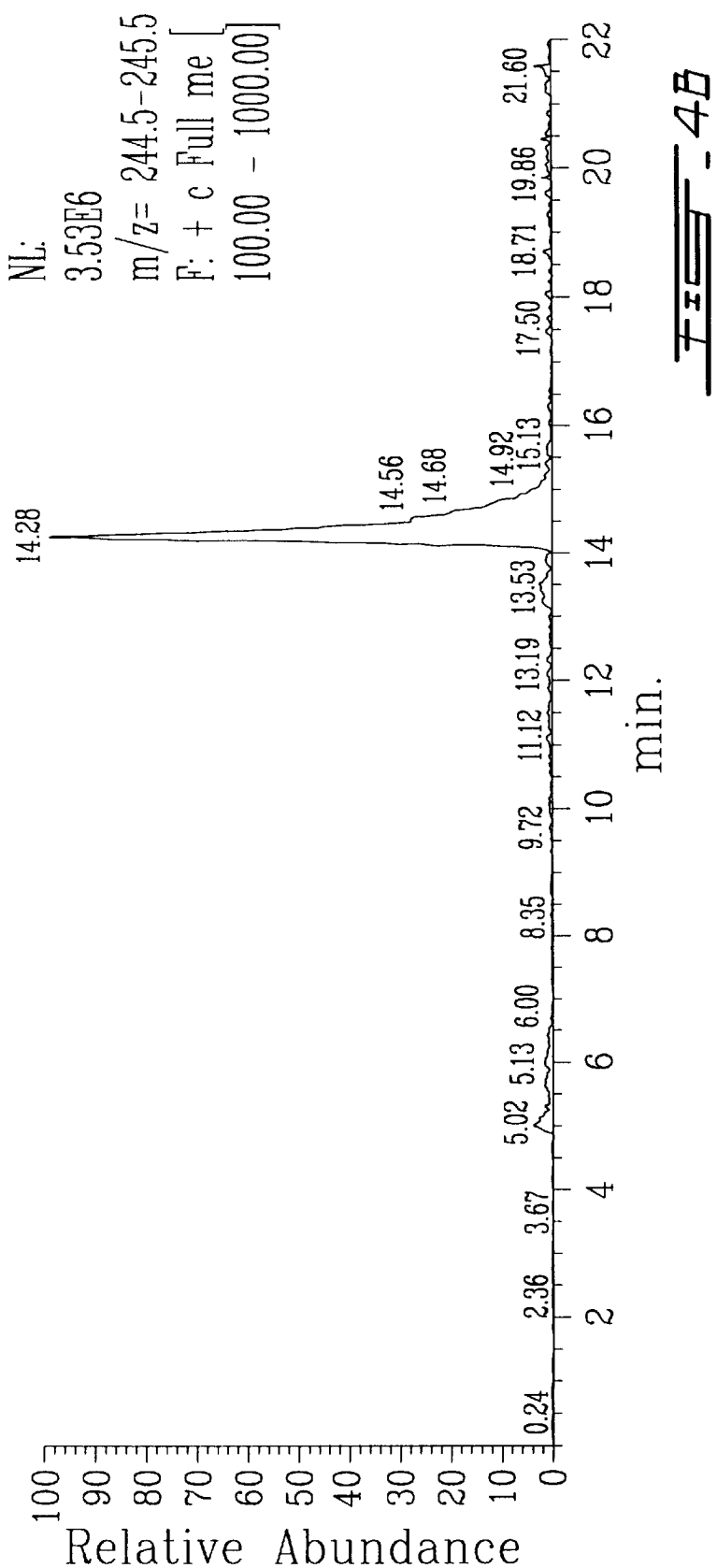

The total ion chromatogram as well as the single chromatogram (245) obtained from analysis of the Æ-986 isolated on the HPLC NH2 system (ammonium formate acid pH 3 gradient) are presented in FIG. 4. The Æ-986 was detected in fractions collected between 14 to 16 minutes corresponding to a 14.28 minutes retention time for elution of the m/e 245 peak.

In negative mode (Table 14) only, ions 243 and 289 were detected in the region of interest (Æ-986) in all the chromatographic system evaluated. Again perfect co-elution of those two ions suggest the formation of a formate adduct on the ion 243. This phenomenon is observed frequently in negative ion when ammonium formate is used as buffer in the mobile phase. This was proven by replacing the ammonium formate buffer with an ammonium acetate buffer at the same pH. The ammonium acetate mobile phase was post column alkalinized with ammonium hydroxide solution prior to MS detection. Both systems showed a clear signal for the ion 243 but ion 289 was only detected in the formate system and a new ion (303) corresponding to an acetate adduct was detected in the second chromatographic system.

Accordingly, it is believed that the Æ-986 component has a molecular weight of about 244 amu (243 equivalent to the M−1 species in the negative ion mode).

TABLE 13

Positive ion detection

| | CHROMATOGRAPHIC CONDITION | | | | | | |
|---|---|---|---|---|---|---|---|
| DESCRIPTION | ISOCRATIC C 18 NEUTRAL CONDITION (AM. FORMATE) | ISOCRATIC C 15 NEUTRAL CONDITION (AM. FORMATE) | ISOCRATIC C 18 NEUTRAL CONDITION (AM. FORMATE) | GRADIENT C 18 ACID CONDITION (AM. FORMATE) | ISOCRATIC C 18 ACID CONDITION (AM. FORMATE) | GRADIENT NH2 ACID CONDITION (AM. FORMATE) | ISOCRATIC C 18 ACID CONDITION (AM. FORMATE) |
| Fraction collection | Collection 2F1: 15 to 1.5 min. F20: 24.5 to 25 min | Collection 3F1: 15 to 15.5 min. F20: 24.5 to 25 min | Collection 5F1: 12 to 12.5 min F20: 21.5 to 22 min | Collection 7F1: 12 to 12.5 min. F20: 21.5 to 22 min | Collection 9F1: 6 to 7 min. F20: 23 to 24 min | F.P.4F1: 7 to 8 min. F15: 21 to 22 min | Collection 10F1: 6 to 6.5 min. F20: 25.5 to 26 min |

TABLE 13-continued

Positive ion detection

| | CHROMATOGRAPHIC CONDITION | | | | | | |
|---|---|---|---|---|---|---|---|
| DESCRIPTION | ISOCRATIC C 18 NEUTRAL CONDITION (AM. FORMATE) | ISOCRATIC C 15 NEUTRAL CONDITION (AM. FORMATE) | ISOCRATIC C 18 NEUTRAL CONDITION (AM. FORMATE) | GRADIENT C 18 ACID CONDITION (AM. FORMATE) | ISOCRATIC C 18 ACID CONDITION (AM. FORMATE) | GRADIENT NH2 ACID CONDITION (AM. FORMATE) | ISOCRATIC C 18 ACID CONDITION (AM. FORMATE) |
| GIA activity | ND | N.E | 13.5 to 14 min: 49 14 to 14.5 min: 24 14.5 to 15 min: 8 | 16.5 to 17 min: 36 | 16 to 17 min: 32 17 to 18 min: 13 | 14 to 15 min: 68 15 to 16 min: 8 | 16 to 16.5 min: 12 16.6 to 17 min: 29 17 to 17.5 min: 8 |
| Expected R.T. | 13 to 15 min. | 13 to 15 min. | 14 min. | 16.5 min. | 16.8 min. | 14.5 min. | 16.8 min. |
| m/e Detect | 191 227 229 245 334 346 684 706 | 191 227 229 245 334 346 684 706 | 191 227 229 245 334 — 684 706 | — 227 229 245 — — 684 706 | — 227 229 245 — — — — | — 227 — 245 — — — — | — 227 229 245 — — — — |

TABLE 14

Negative ion detection

| | CHROMATOGRAPHIC CONDITION | | | | | | |
|---|---|---|---|---|---|---|---|
| DESCRIPTION | ISOCRATIC C 18 NEUTRAL CONDITION (AM. FORMATE) | ISOCRATIC C 18 NEUTRAL CONDITION (AM. FORMATE) | ISOCRATIC C 18 NEUTRAL CONDITION (AM. FORMATE) | ISOCRATIC C 18 ACID CONDITION (AM. FORMATE) | GRADIENT NH2 ACID CONDITION (AM. FORMATE) | ISOCRATIC C 18 ACID CONDITION (AM. FORMATE) | ISOCRATIC C 18 ACID CONDITION (AM. ACETATE) |
| Fraction collection | Collection 4F1: 15 to 15.5 min. F20: 24.5 to 25 min | Collection 6F1: 12 to 12.5 min. F20: 21.5 to 22 min | Collection 11F1: 6 to 7 min. F18: 23 to 24 min | Collection 12F1: 6 to 6.5 min. F34: 22.5 to 23 min | Collection 13F1: 6 to 7 min. F22: 27 to 28 min | F.P.2F1: 7 to 8 min. F17: 23 to 24 min | — |
| GIA activity | ND | 14 to 14.5 min: 17 14.5 to 15 min: 10 15 to 15.5 min: 8 | 16 to 17 min: 27 17 to 19 min: 39 | 16 to 16.5 min: 7 16.6 to 17 min: 17 17 to 17.5 min: 18 | 13 to 14 min: 14 14 to 15 min: 1 | 18 to 19 min: 69 | N.A. |
| Expected R.T. | 13 to 15 min. | 14 min. | 17 min. | 17 min. | 14 min. | | |
| m/e Detect | 145 189 243 289 682 683 | 145? 189 243 289 682 683 | — — 243 289 — — | — — 243 289 — — | — 227 243 289 — — | — — 243 289 — — | — — 243 — — — |

Empirical Formula and Partial Structure Elucidation of Æ-986 LC-MS empirical formula determination Mass spectrometry was used to obtain information regarding the structure of Æ-986. Table 15 summarizes the conditions used in the LC-MS analysis of Æ-986.

TABLE 15

Chromatographic conditions used for LC-MS partial empirical formula determination:

| | |
|---|---|
| Column | C18 ODS-2, 5u, 4.6 × 250 mm, Phenomenex |
| Column temperature | 30° C. |

TABLE 15-continued

Chromatographic conditions used for LC-MS partial empirical formula determination:

| | |
|---|---|
| Flow rate | 0.7 ml/min. |
| Injection volume | 100 μl of purified fraction |
| Eluant | Ammonium formate (0.01 M, pH 3)/ methanol (75:25) |
| Elution mode | Isocratic |
| Detection | UV: 205 nm, 254 nm, MS |
| Run time | 25 min. |
| Fraction collection | each min. or 30 sec. with different delay time. |

The determination of the isotopic ratio of 247, 246, 245 was conducted in zoom scan mode to increase the precision on the reading of the weak signal of those ions. The isotopic ratios obtained for the ion 246/245 (A+1 type) and 247/245 (A+2 type) are presented in a table format below.

Ratio of 5.9% of the m/e 247/245 peak heights (A+2 isotopic ratio) strongly suggest the presence of a sulfur and few oxygen atoms on the molecule.

Isotopic ratio of 11.8% for the A+1 elements (m/e 246/245 peak height) can account for up to 10 carbon or a mixture of carbon, nitrogen and sulfur (1) on the molecule.

With a molecular weights of 244 amu only an even number of nitrogen (0,2,4) can be present on this molecule.

LC/MSn Structural Elucidation

A partial elucidation of the structure of the Æ-986 was done by conducting tandem mass spectrometry experiments.

TABLE 16

Chromatographic condition used for MSn experiment are described below:

| | |
|---|---|
| Column | C18 ODS-2, 5u, 4.6 × 250 mm, Phenomenex |
| Column temperature | 30° C. |
| Flow rate | 0.7 ml/min. |
| Injection volume | 100 µl of purified fraction |
| Eluant | Ammonium formate (0.01 M. pH 3)/methanol (75:25) |
| Elution mode | Isocratic |
| Detection | UV: 205 nm, 254 nm, MS |
| Run time | 25 min. |
| Fraction collection | each min. or 30 sec. with different delay time. |

Tandem mass spectrometry (MS/MS) experiments which were conducted on positive ions for the molecular ion 245 m/e (M+1) showed losses of 18 amu (m/e 227.1) and 36 amu (m/e 209) (minor). Those losses correspond to the loss of one and two molecules of water ($-H_2O$ and $-2H_2O$, respectively), indicating the presence of an alcohol, and/or diol moiety in Æ-986. The actual MS/MS spectrum is presented in FIG. 5.

Figure 6:
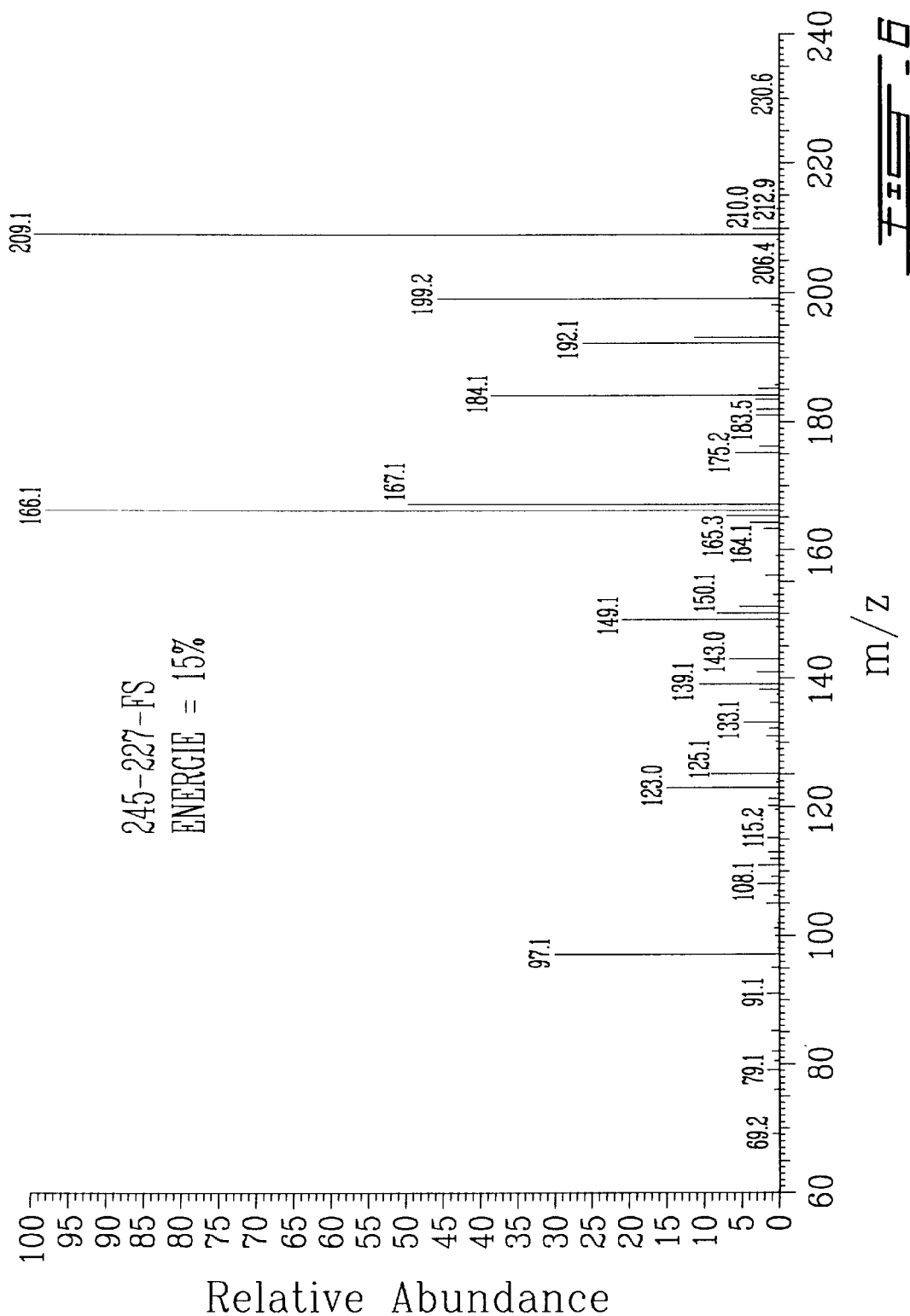
FIG. 6 depicts the MS/MS spectrum of the specific fragments of the ion 227 (245 M+1 minus a water molecule).

An MS/MS experiment conducted on the m/e 227 ion resulted in a complex spectrum with many characteristic fragments of the Æ-986 chemical structure. Fragments appearing in this spectrum could result from either one or both fragmentation of the m/e 227 ion or fragmentation of other intense ions appearing in this spectrum (i.e. m/e 166 is from fragmentation of the 209 ion). Consequently, further MS/MS experiments were conducted on selected fragments of the m/e 227 ion. The MS/MS spectrum obtained is depicted in FIG. 6.

An MS/MS experiment on the 209 m/e ion (M+1-$2H_2O$) results from a loss of 60 amu, to give m/e 149 which is characteristic of a loss of a carboxylic acid ($-CH_3COOH$) moiety.

The ion 149 m/e (M+1-$2H_2O$ —$CH_3COOH$) was then reanalyzed by MS/MS and the following fragments were obtained: m/e 105, 115, 116 and 134. Loss of 15 from 149 to 134 most likely corresponds to the loss of $CH_3$. Loss of 33 and 34 are characteristic of the loss of SH and $H_2S$ therefore strongly suggesting the presence of a sulfur-containing group (thiol or thioether) in Æ-986. Loss of 44 from m/e 149 to 105 can be due to losses of several different groups.

Chemical Derivatization Structural Elucidation

The Æ-986 was subject to conditions commonly used for the esterification of of carboxylic acids as detailed below.

Methylation (HCl/Methanol)

For methylation of purified fractions, the present inventors evaporated 15 µl of a purified fraction (4000×) of Æ-986 and added 100 µl of a mixture HCl (12 N):MeOH/ (1:99) in a closed vial. The mixture was incubated 60–90 min, at 45° C., then evaporated to dryness and dissolved in 100 µl of water. This solution was injected according to chromatographic conditions used for LC/MS structure elucidation.

Methylation ($BF_3$/methanol)

For methylation of purified fractions, the present inventors evaporated 15 µl of purified fraction (4000×) of Æ-986 and added 100 µl of $BF_3$/methanol solution in a closed vial. The mixture was incubated 60–90 min. at 45° C., then evaporated to dryness and dissolved with 100 µl of water. This solution was injected according to chromatographic conditions used for LC/MS structure elucidation.

Dilution of purified fractions (4000×)

To verify the recovery of derivatization, the present inventors diluted 15 µl of a purified fraction (4000×) of Æ-986 with 85 µl of water. The diluted solution was analyzed according to the chromatographic conditions used for LC/MS elucidation.

Results

Derivatization of the of Æ-986 component with $BF_3$/methanol or H+/methanol at 45° C. for one hour resulted in the disappearance of its chromatographic signal, as determined by signal strength at the expected retention time for the of Æ-986, by more than 95%. These two reactions are well known for the transformation of carboxylic acid to their corresponding methyl esters. Methylation causes an increase in the molecular weight of the Æ-986 as well as an increase of its retention time on the chromatographic system. The concentration of the Æ-986 derivatives produced herein did not allow the detection of the derivatized product.

Physicochemical Properties

The presence of a weak acidic functional group, such as a carboxylic acid, on the Æ-986 was confirmed by an increase of its retention time on the HPLC C18 column when pH of the formate buffer was decreased from 7 to 3. This strongly suggests that a moiety possessing a pKa of about 4 or more is present in the Æ-986.

If a thiol or thioether functional group is present in the Æ-986, as suggested by the MS/MS data, it will affect the recovery of the Æ-986 from the 0-500 fraction and the cartilage. It is likely that only the free thiol portion of the Æ-986 can be extracted according to the present process as thiols tend to form disulfide (S=S) bonds with other sulfur containing molecules (such as proteins, peptide, amino acid) in solution. The formation of a disulfide adduct generally alters the physicochemical properties of the molecules containing thiol groups and affect their recovery by extraction.

It is possible that a disulfide adduct of Æ-986 may not be isolated by direct extraction of the 0-500 fraction (20×). The formation of disulfide adducts of the Æ-986 can be minimized by treating solutions containing it with tributylphosphamide at pH 7 and room temperature for 15 minutes prior to extractions, especially those at pH 3 (SPE C18 pH 3). Other disulfide bond-cleaving reagents, such as dithiothreitol and β-mercaptoethanol, can be used to minimize the formation of disulfide adducts of Æ-986.

The above processes for the recovery and the isolation of biological activities from shark cartilage can be adapted to any source of cartilage (1) to extract fractions exhibiting desired biological activities, and (2) to extract specific components possessing those biological activities.

Since the present invention teaches that biologically active components may be extracted from cartilage in a variety of hydrophilic solvents, the above processes can be adapted to extract biologically active components from cartilage of different species. Any component isolated from a cartilage material, preferably shark cartilage, and: 1) possessing a biological activity profile similar to or the same as that of the Æ-986 component; and/or 2) having a mass of 244 amu, is considered within the scope of the present invention.

This invention has been described hereinabove, with reference to specific embodiments. It is well within the ability of the skilled artisan to make modifications without departing from the above teachings. These modifications are within the scope of this invention as defined in the appended claims.

What is claimed is:

1. A process for obtaining a soluble component from cartilage comprising the steps of:
   a) treating cartilage material with a quantity of organic solvent-containing solution to form a first mixture comprising a soluble component of cartilage wherein the organic solvent-containing solution comprises 1–100% by volume of ethanol or methanol; and
   b) separating said first mixture to form a first liquid extract comprising said soluble component and a first mass of solids, wherein said soluble component possesses at least anti-matrix metalloprotease activity.

2. The process of claim 1 further comprising the steps of:
   a) removing a sufficient amount of liquid from said first liquid extract to form a substantially dry second mass of solids;
   b) treating said second mass of solids with water to form a second mixture; and
   c) separating said second mixture to form a final liquid extract and a third mass of solids, wherein said final liquid extract comprises said soluble component.

3. The process of claim 2 wherein said removing of liquid is done by one or more of evaporation, lyophilization, distillation, azeotropic distillation, desiccation, liquid/liquid extraction, addition of organic solvent absorbent and rotary evaporation.

4. The process of claim 2 wherein said final liquid extract further comprises a stabilizing agent.

5. The process of claim 4 wherein said stabilizing agent is sucrose.

6. The process of claim 1 further comprising the step of:
   removing substantially all of said organic solvent from said first liquid extract.

7. The process of claim 1 wherein said first mixture is separated by one or more of centrifugation, filtration, dialysis and settling of solids followed by removal of a supernatant.

8. The process of claim 1 wherein said cartilage material is shark cartilage.

9. The process of claim 1 further comprising the step of:
   homogenizing said cartilage material prior to, during or after treatment of said cartilage material with organic solvent-containing solution.

10. The process of claims 1 or 9 wherein said organic solvent-containing solution further comprises water.

11. The process of claim 9 wherein said homogenizing is done by one or more of physical and chemical means.

12. The process of claim 1 further comprising the steps of:
   a) treating said first mass of solids with a quantity of organic solvent-containing solution to form a second mixture comprising a soluble component of cartilage; and
   b) separating said second mixture to form a second liquid extract comprising said soluble component and a second mass of solids.

13. The process of claim 12 further comprising the steps of:
   a) treating said second mass of solids with a quantity of organic solvent-containing solution to form a third mixture comprising a soluble component of cartilage; and
   b) separating said third mixture to form a third liquid extract comprising said soluble component and a third mass of solids.

14. The process of claim 13 further comprising the step of:
   combining said first, second and third liquid extracts to form a total liquid extract.

15. The process of claim 1, wherein said soluble component is isolated from said first liquid extract.

16. The process of claim 1 wherein said first liquid extract further comprises a stabilizing agent.

17. The process of claim 16 wherein said stabilizing agent is sucrose.

* * * * *